(12) United States Patent
Norieda

(10) Patent No.: US 9,910,528 B2
(45) Date of Patent: Mar. 6, 2018

(54) TACTILE FORCE SENSE PROVIDING APPARATUS, INFORMATION TERMINAL, TACTILE FORCE SENSE PROVIDING METHOD, AND COMPUTER READABLE RECORDING MEDIUM

(71) Applicant: NEC Corporation, Tokyo (JP)

(72) Inventor: Shin Norieda, Tokyo (JP)

(73) Assignee: NEC Corporation, Tokyo (JP)

( * ) Notice: Subject to any disclaimer, the term of this patent is extended or adjusted under 35 U.S.C. 154(b) by 2 days.

(21) Appl. No.: 15/021,875

(22) PCT Filed: Sep. 2, 2014

(86) PCT No.: PCT/JP2014/073044
§ 371 (c)(1),
(2) Date: Mar. 14, 2016

(87) PCT Pub. No.: WO2015/045755
PCT Pub. Date: Apr. 2, 2015

(65) Prior Publication Data
US 2016/0224167 A1 Aug. 4, 2016

(30) Foreign Application Priority Data

Sep. 26, 2013 (JP) ................................ 2013-199728

(51) Int. Cl.
G06F 3/041 (2006.01)
A61B 5/22 (2006.01)
G06F 1/16 (2006.01)

(52) U.S. Cl.
CPC ............ *G06F 3/0414* (2013.01); *A61B 5/225* (2013.01); *G06F 1/1626* (2013.01); *G06F 2203/0331* (2013.01)

(58) Field of Classification Search
CPC ................ G06F 3/0414; G06F 1/1626; G06F 2203/0331; A61B 5/225
(Continued)

(56) References Cited

U.S. PATENT DOCUMENTS 5,778,885 A * 7/1998 Doyama ................ A61B 5/225
600/595

FOREIGN PATENT DOCUMENTS

EP 626634 A2 11/1994
JP S62-2621222 A 11/1987
(Continued)

OTHER PUBLICATIONS

International Search Report corresponding to PCT/JP2014/073044, dated Oct. 28, 2014, 3 pages.
(Continued)

*Primary Examiner* — Mark Regn
(74) *Attorney, Agent, or Firm* — Wilmer Cutler Pickering Hale and Dorr LLP

(57) ABSTRACT

An information terminal is provided with a display device, a position detection unit that detects the position of a portion receiving a tactile force sense, an information processing unit that changes content according to the detected position and calculates the tactile force sense on the basis of the changed content, and a tactile force sense providing device. The tactile force sense providing device includes a fitting member including an operation input unit, a conveyance member that conveys a force via the fitting member, a drive unit that produces the force to the conveyance member, and a control unit that provides a tactile force sense by increasing or reducing an initial force, and outputs a signal to the information processing unit according to input from the
(Continued)

operation input unit by a user. The information processing unit changes content according to the signal from the control unit.

12 Claims, 13 Drawing Sheets

(58) Field of Classification Search
USPC .......................................................... 345/173
See application file for complete search history.

(56) References Cited

FOREIGN PATENT DOCUMENTS

| | | |
|---|---|---|
| JP | H07-146751 A | 6/1995 |
| JP | 2001-133300 A | 5/2001 |
| JP | 2002-304246 A | 10/2002 |
| JP | 2003-015810 A | 1/2003 |
| JP | 2003015810 A * | 1/2003 |
| JP | 2003-308141 A | 10/2003 |

OTHER PUBLICATIONS

Written Opinion with English Translation corresponding to PCT/JP2014/073044, dated Oct. 28, 2014, 9 pages.
Inoue Masaharu, Hasegawa Shoichi, Kim Seahak, Sato Makoto, "A New Force Computation Method for Wire Driven Force Display", IEICE Technical Report, Jun. 4, 2001 vol. 101, No. 109, pp. 1-6.

* cited by examiner

TACTILE FORCE SENSE PROVIDING APPARATUS, INFORMATION TERMINAL, TACTILE FORCE SENSE PROVIDING METHOD, AND COMPUTER READABLE RECORDING MEDIUM

CROSS-REFERENCE TO RELATED APPLICATIONS

This application is a national stage application of International Application No. PCT/JP2014/073044 entitled "SENSE OF TACTILE FORCE PRESENTATION DEVICE, INFORMATION TERMINAL, SENSE OF TACTILE FORCE PRESENTATION METHOD, AND COMPUTER READABLE RECORDING MEDIUM," filed on Sep. 2, 2014, which claims the benefit of the priority of Japanese Patent Application No. 2013-199728 filed on Sep. 26, 2013, the disclosures of each of which are hereby incorporated by reference in their entirety.

TECHNICAL FIELD

The present invention relates to a tactile force sense providing apparatus that presents (conveys) a tactile force sense to a user, a tactile force sense providing system and a tactile force sense providing method that include the tactile force sense providing apparatus, and a computer-readable recording medium that records a program to achieve the tactile force sense providing apparatus, the tactile force sense providing system, and the tactile force sense providing method.

BACKGROUND ART

Ordinarily, on an input apparatus having a screen of which input operations are performed, such as a touch panel, feedback to a user in accordance with the operations has been performed through only information by use of display indication or sound. Since, on a case using such an input apparatus, a user is unable to obtain the same feedback as a sense of clicking of a real key for an input operation, even when the user presses a software keyboard displayed on a display. Therefore, the user is unable to recognize what the user is touching under his/her finger. As a result, a problem is caused in that the user is unable to obtain information of a content and it is thus difficult for the user to use the apparatus.

To handle such a problem, tactile force sense providing apparatuses that provide tactile force senses in accordance with operations to users have been developed in the past (for example, refer to PTL1 and PTL2). For example, PTL1 discloses a tactile force sense providing apparatus mounted on a wrist of an operator. The tactile force sense providing apparatus disclosed in PTL1 is configured with a fulcrum unit mounted on the wrist, a grip unit that the user grips, and a plurality of wires that interconnect the fulcrum unit and the grip unit. In the tactile force sense providing apparatus disclosed in PTL1, the fulcrum unit has a function to pull the wires, and by adjusting tensile forces in the respective wires, a tactile force sense is provided to the user, via the grip unit.

PTL2 discloses a glove-type tactile force sense providing apparatus. The tactile force sense providing apparatus disclosed in PTL2 has frames attached along the respective fingers of a glove. Each frame has linkage mechanisms attached to positions corresponding to joints of a finger, and, further, each linkage mechanism has a motor attached to drive the frame. Thus, the tactile force sense providing apparatus disclosed in PTL2, is able to provide a tactile force sense to a hand of a user on which the glove is worn, via the frames, by operating motors operate in accordance with details of a content.

CITATION LIST

Patent Literature

[PTL1]: Japanese Unexamined Patent Application Publication No. 2002-304246

[PTL2]: Japanese Unexamined Patent Application Publication No. 2003-308141

SUMMARY OF INVENTION

Technical Problem

However, for the tactile force sense providing apparatus disclosed in PTL1, there is a problem that the tactile force sense can be provided only in the case that the user takes simple actions, such as touching and hitting, to an object existing in a virtual space.

On the other hand, since, by using the tactile force sense providing apparatus disclosed in PTL2, a tactile force sense is provided to respective fingers of the user, the user is able to take complicated actions, such as grabbing, releasing, throwing, and catching. By using such a tactile force sense providing apparatus, it is also possible to provide the tactile force sense for actions described above. However, for the tactile force sense providing apparatus disclosed in PTL2, complicated linkage mechanisms are required to be implemented with respect to each finger, which causes a problem, that the size of an apparatus becomes larger.

For both the tactile force sense providing apparatus disclosed in PTL1 and the tactile force sense providing apparatus disclosed in PTL2, there is another problem that the apparatuses cannot be mounted on portable terminal apparatuses, due to the structure of the apparatus.

An example of an object of the present invention is to provide a tactile force sense providing apparatus, an information terminal, a tactile force sense providing method, and a computer-readable recording medium that solve the above-described problems and enable to improve the degree of freedom of actions taken by a user, while downsizing the apparatus.

Solution to Problem

To achieve the object of the present invention, a tactile force sense providing apparatus according to one aspect of the present invention includes: a fitting member that is formed so as to be attached on a portion of the user that receives the tactile force sense to be provided, and includes an operation input unit to input an operation performed by the user; a conveyance member that extends from the apparatus to the fitting member and conveys a force in a pulling direction to the user via the fitting member; a drive unit that produces the force in the pulling direction and provides the produced force to the conveyance member; and a control unit that is configured to produce the force in the pulling direction of a preset magnitude to the drive unit as an initial force in advance, increase or decrease the initial force so that the tactile force sense required to be provided is provided to the user via the fitting member on providing the tactile force sense, and, when the user inputs an operation via the operation input unit, further output a signal in accordance with the input operation.

To achieve the object of the present invention, an information terminal according to one aspect of the present invention includes: a display apparatus that displays the content on the screen; a position detection unit that detects a position of a portion of the user that receives the tactile force sense to be provided; an information processing unit that changes details of the content in accordance with the detected position and, on the basis of the changed details of the content, calculates a tactile force sense required to be provided; and a tactile force sense providing apparatus, the tactile force sense providing apparatus including: a fitting member that is formed so as to be attached on a portion of the user that receives the tactile force sense to be provided and includes an operation input unit to input an operation performed by the user; a conveyance member that extends from the information terminal to the fitting member and conveys a force in a pulling direction to the user via the fitting member; a drive unit that produces the force in the pulling direction and providing the produced force to the conveyance member; and a control unit that is configured to produce the force in the pulling direction of a preset magnitude as an initial force to the drive unit in advance, increase or decrease the initial force so that the calculated tactile force sense is provided to the user via the fitting member on providing the tactile force sense calculated by the information processing unit, and when the user inputs an operation via the operation input unit, further output a signal in accordance with the input operation to the information processing unit, and, the information processing unit changing details of the content in accordance with details of the signal, when the control unit outputs the signal.

To achieve the object of the present invention, a tactile force sense providing method according to one aspect of the present invention is a method to provide a tactile force sense to a user in accordance with details of a content displayed on a screen, that includes, by using an apparatus including a fitting member that is formed so as to be attached on a portion of the user that receives the tactile force sense to be provided and includes an operation input unit to input an operation performed by the user, a conveyance member that extends to the fitting member and conveys a force in a pulling direction to the user, and a drive unit that produces the force in the pulling direction and provides the produced force to the conveyance member: (a) a step of producing a force in a pulling direction of a preset magnitude to the drive unit as an initial force in advance; (b) a step of increasing or decreasing the initial force so that the tactile force sense to be provided is provided to the user via the fitting member on providing the tactile force sense; and (c) a step of, when the user inputs an operation via the operation input unit, outputting a signal in accordance with the input operation.

To achieve the object of the present invention, a computer-readable recording medium according to one aspect of the present invention is a recording medium storing a program including instructions for a computer included in an apparatus to provide a tactile force sense to a user in accordance with details of a content displayed on a screen. The apparatus includes a fitting member that is formed so as to be attached on a portion of the user that receives the tactile force sense to be provided and includes an operation input unit to input an operation performed by the user, a conveyance member that extends to the fitting member and conveys a force in a pulling direction to the user, a drive unit that produces the force in the pulling direction and provides the produced force to the conveyance member, and the computer. And the program allowing the computer to execute: (a) a step of producing a force in a pulling direction of a preset magnitude to the drive unit as an initial force in advance; (b) a step of increasing or decreasing the initial force so that the tactile force sense to be provided is provided to the user via the fitting member on providing the tactile force sense; and (c) a step of, when the user inputs an operation via the operation input unit, outputting a signal in accordance with the input operation.

Advantageous Effects of Invention

As described above, according to the present invention, it is possible to improve the degree of freedom of actions taken by a user while downsizing an apparatus.

DESCRIPTION OF EMBODIMENTS (Embodiment)

Hereinafter, a tactile force sense providing apparatus, an information terminal, a tactile force sense providing method, and a program in an exemplary embodiment of the present invention will be described with reference to FIGS. 1 to 13.

[Apparatus Configuration]

Figure 1:
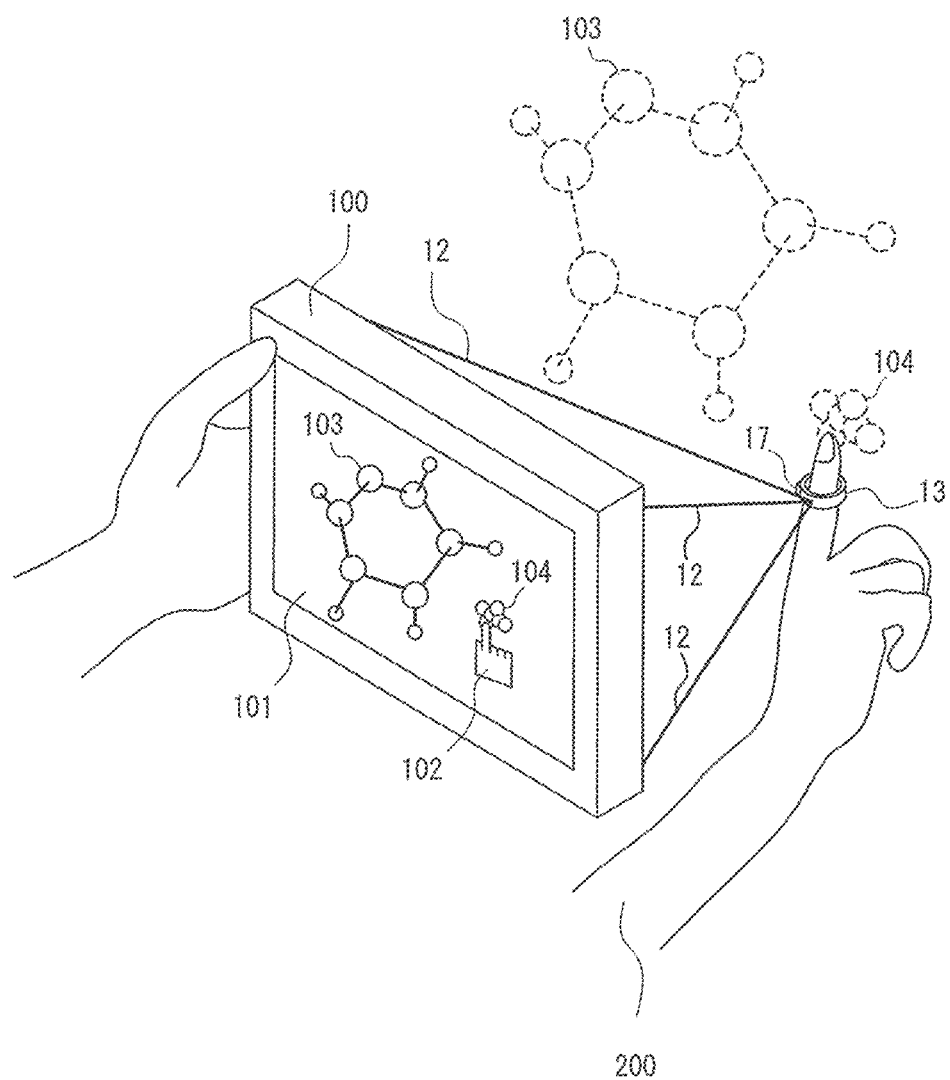
FIG. 1 is a perspective view illustrating an external appearance of an information terminal in an exemplary embodiment of the present invention.
Figure 2:
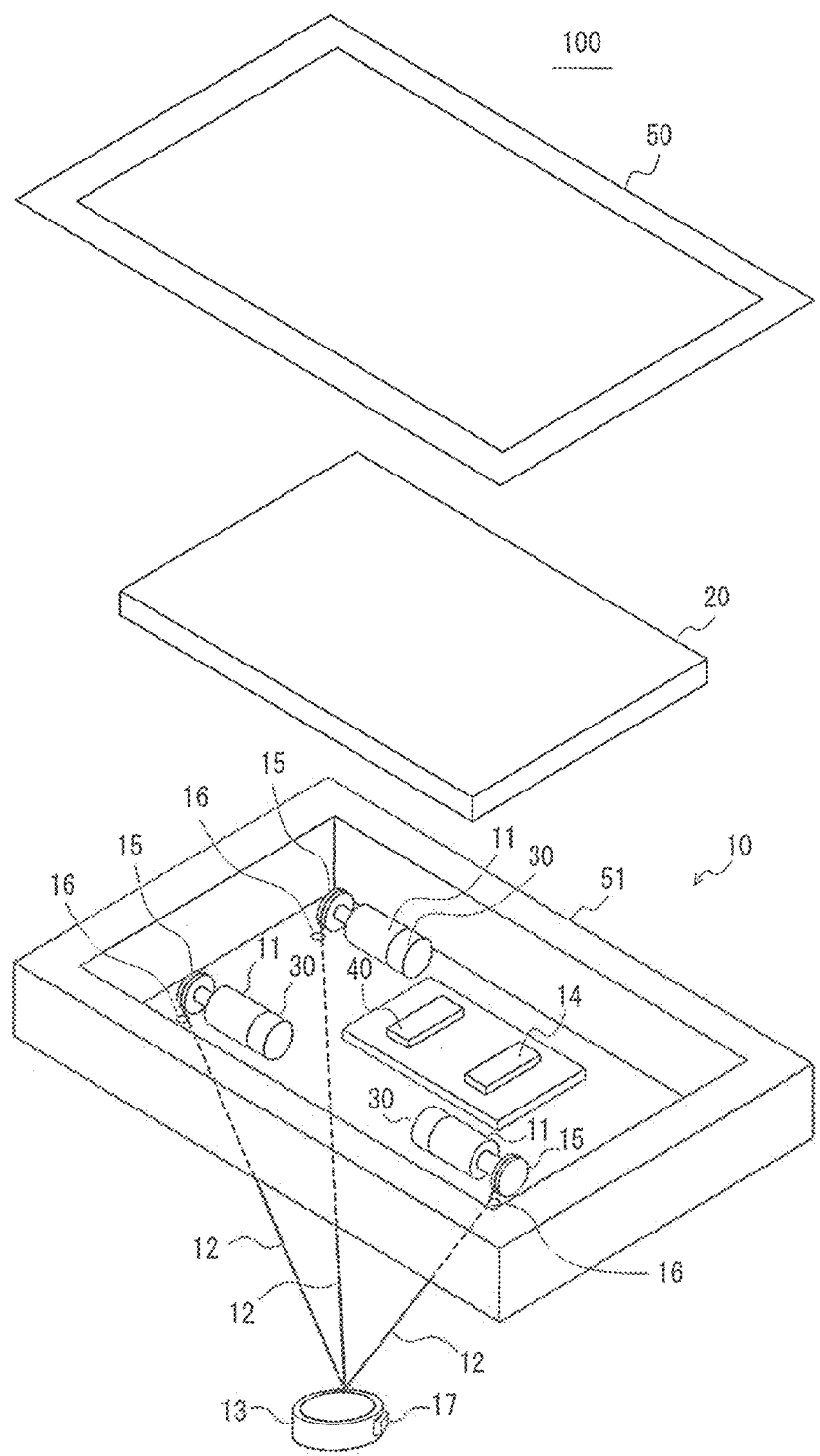
FIG. 2 is an exploded perspective view illustrating respective components of the information terminal in the exemplary embodiment of the present invention.

First, with reference to FIGS. 1 and 2, configurations of the tactile force sense providing apparatus and the information terminal in the exemplary embodiment will be described. FIG. 1 is a perspective view illustrating an external appearance of the information terminal in the exemplary embodiment of the present invention. FIG. 2 is an disassembled perspective view illustrating respective components of the information terminal in the exemplary embodiment of the present invention.

With reference to FIG. 1, a configuration of the external appearance of the information terminal in the exemplary embodiment will be described. As illustrated in FIG. 1, an information terminal 100 in the exemplary embodiment is a tablet-type information terminal, and, as illustrated in FIG. 2, which will be described later, includes the tactile force sense providing apparatus that provides a tactile force sense to a user 200. The tactile force sense providing apparatus includes a fitting member 13 that is formed so as to be attached on a portion of the user 200 that receives a tactile force sense provided.

In the exemplary embodiment, the information terminal 100 is capable of detecting a position of the portion of the user 200 that receives a tactile force sense, or specifically, a finger on which the fitting member 13 is attached, in a space on the rear side of the terminal (the opposite side to a side on which a screen 101 is mounted). With this, the user 200 is able to perform an input operation to the information terminal 100 by moving the position of the finger.

The information terminal 100 is capable of displaying a virtual space on the screen 101. Further, the information terminal 100 is also capable of displaying an object (hereinafter, referred to as "user object") 102 corresponding to the finger of the user 200 in the virtual space, in accordance with the detected position. When a virtual object 103 or 104 arranged in the virtual space comes into contact with the user object 102, the tactile force sense providing apparatus of the information terminal 100 conveys a feel of touching the virtual object 103 or 104 to the finger of the user 200. In the example in FIG. 1, the virtual objects 103 and 104 are molecular models.

That is, on the information terminal 100, by the user 200 moving his/her finger and/or the virtual objects 103 and 104 moving, movements and states in the virtual space are provided to the user 200, as tactile force senses. In FIG. 1, to illustrate positional relations between the finger of the user 200 and the virtual objects 103 and 104, virtual objects 103 and 104, when assuming that these objects exist in the real space, are illustrated in dashed lines.

With reference to FIG. 2, an internal configuration of the information terminal will be described. As illustrated in FIG. 2, the information terminal includes a display apparatus 20 that displays contents on a screen, position detection units 30, an information processing unit 40, and a tactile force sense providing apparatus 10 that provides a tactile force sense to the user 200 (refer to FIG. 1).

The position detection units 30 detect a position of the portion of the user 200 that receives the provided tactile force sense (the finger on which the fitting member 13 is attached in the example in FIGS. 1 and 2). The information processing unit 40 changes details of contents in accordance with the detected position, and, on the basis of the changed details of the content, calculates a tactile force sense required to be provided to the user.

As illustrated in FIG. 2, the tactile force sense providing apparatus 10 includes the fitting member 13, conveyance members 12, drive units 11, and a control unit 14. The fitting member 13 is, as described above, formed so as to be worn on the portion of the user 200 that receives the tactile force sense provided. The fitting member 13 has an operation input unit 17 to input an operation performed by the user.

Each conveyance member 12 extends from the information terminal 100 to the portion of the user 200 that receives the tactile force sense (the finger in the example in FIGS. 1 and 2) and conveys a force in the pulling direction (hereinafter, referred to as "tensile force") to the user 200. Each drive unit 11 produces a tensile force and provides one of the conveyance members 12 with the produced tensile force.

The control unit 14 controls the drive units 11 to produce tensile forces of predetermined magnitudes set in advance, as initial forces. On providing the tactile force sense calculated by the information processing unit 40, the drive units 11 increase or decrease the initial forces so that the calculated tactile force sense is conveyed to the user 200 via the conveyance members 12 (refer to FIG. 2).

Further, when the user inputs an operation via the operation input unit 17, the control unit 14 outputs a signal to the information processing unit 40 in accordance with the input operation. In this case, the information processing unit 40 changes details of contents in accordance with details of the signal from the control unit 14.

In this way, in the information terminal 100, the tactile force sense providing apparatus 10 provides a tactile force sense by conveying forces in the pulling directions to a finger of the user 200, which is positioned on the rear side of the information terminal 100, via the fitting member 13 and the conveyance members 12. Since the tactile force sense providing apparatus 10 is capable of outputting a signal to the information processing unit 40 in accordance with an operation input by the user via the operation input unit 17, mounted on the fitting member 13, the tactile force sense providing apparatus 10 is able to improve the degree of freedom of actions taken by the user. Since the tactile force sense providing apparatus can be configured to be compact, downsizing of the apparatus can also be achieved. The term "tactile force sense" used in the present invention means resilient force, resistance force, external force, feeling, or the like, that the user senses.

In the following, the configurations of the information terminal 100 and the tactile force sense providing apparatus 10 in the exemplary embodiment will be described further specifically.

As illustrated in FIG. 2, the information terminal 100 includes, in order from the user side, a cover 50, which is formed in a frame-like shape, the display apparatus 20, and a casing 51, which has a box-like shape. The cover 50 is mounted on the opening portion of the casing 51 in such a way that the screen of the display apparatus 20 is exposed. The display apparatus 20 is a thin flat display panel, such as a liquid crystal display panel and an organic EL panel.

The above-described drive units 11, control unit 14, position detection units 30, and information processing unit 40 are arranged on the inside of the casing 51, which is located on the rear side of the display apparatus 20. As illustrated in FIG. 2, in the exemplary embodiment, three conveyance members 12 are used, and, in correspondence thereto, three drive units 11 are arranged.

In the exemplary embodiment, each of the conveyance members 12 is string-like members, such as wires, that extend from different positions on the rear side of the information terminal 100 to the portion (finger) of the user 200 that receives the tactile force sense provided. A tip of each conveyance member 12 is fixed to the fitting member 13, which is worn on the portion of the user 200 that receives the tactile force sense provided.

Further, in the exemplary embodiment, the fitting member 13 is formed as a ring shape that can be worn on a finger of the user 200. A switch is mounted on the fitting member 13 as the operation input unit 17. The user is able to input an operation by turning on and off the switch, which functions as the operation input unit 17. In the following description, there is a case in which the operation input unit 17 is referred to as "switch 17".

In the exemplary embodiment, each drive unit 11 is a motor the shaft of which is attached with a pulley 15. And, by winding in a corresponding conveyance member 12 around the pulley 15, the drive unit 11 provides the corresponding conveyance member 12 with a force in the pulling direction. One end of each conveyance member 12 is fixed to the pulley.

Further, a through hole 16 is formed on the bottom of the casing 51 with respect to each conveyance member 12, and each conveyance member 12 extends to the rear side of the information terminal 100 via a through hole 16. While the position of each through hole 16 is not particularly limited to a specific position, a presentation range of tactile force senses is determined on the basis of the positions of the respective through holes 16, as described later (refer to an area "X" in FIG. 8). Thus, the positions of the respective through holes 16 are determined by taking the required presentation range into consideration.

As described above, in the exemplary embodiment, a "presentation force" is provided to the finger of the user 200, by the fitting member 13 being pulled by three conveyance members 12 (refer to FIG. 1). That is, a tactile force sense is provided through a resultant force of tensile forces that the respective drive units 11 provide to the conveyance members 12.

Two out of three conveyance members 12 function as wiring that connects the switch 17 to the control unit 14. Specifically, in the example in FIG. 2, a conductive wire, of which the one end is connected to the switch 17, is installed inside each conveyance member 12 that functions as wiring. Further, although not illustrated in FIG. 2, the other end of each conductive wire extends beyond the fixing portion of a conveyance member 12 to a pulley to the control unit 14.

In the exemplary embodiment, each position detection unit 30 is an encoder that is attached to the shaft of each drive unit 11. Thus, the position detection unit 30 outputs data identifying a rotation number of the shaft of the motor to the information processing unit 40, as data to detect the position of the portion of the user that receives the tactile force sense provided (hereinafter, referred to as "position detection data").

When the information processing unit 40 receives the position detection data output from the respective position detection units 30, the information processing unit 40 calculates lengths of the respective conveyance members 12 from the corresponding through holes 16 to the fitting member 13, on the basis of the total lengths of the conveyance members 12, the diameters of the pulleys 15, the distances from the respective pulleys 15 to the corresponding through holes 16, and so on, which have been registered in advance. On the basis of the calculated lengths of the respective conveyance members 12, the information processing unit 40, as will be described later, calculates a position of the portion of the user 200 that receives the tactile force sense provided, that is, a position of the fitting member 13.

In the exemplary embodiment, the control unit 14 and the information processing unit 40 are individually achieved by computers, such as microcomputers. Both the control unit 14 and the information processing unit 40 may be implemented by use of different computers, or an identical computer.

As described above, in the exemplary embodiment, a string-like member (conveyance member 12) is used as a conveyance mechanism of force produced by a motor, which functions as the drive unit 11, as illustrated in FIG. 2. Since, for this reason, weight of component members of the tactile force sense providing apparatus 10 can be reduced, and a mechanism, of the tactile force sense providing apparatus 10, to provide a tactile force sense can be simplified, therefore, a reduction in size and weight of the information terminal 100 is achieved.

In the exemplary embodiment, the conveyance directions of tensile forces by the conveyance members 12 can be set freely through position arrangement of the pulleys 15 and the through holes 16. Further, the distances from the through holes for the conveyance members 12 to the fitting member 13 can be set freely on the basis of the winding amounts of the corresponding pulleys 15. Since, for this reason, the range in which the user is able to move his/her finger can be set large, the tactile force sense providing apparatus 10 is able to provide a three-dimensional tactile force sense over a wide range. Since light string-like members are used as the conveyance members 12, it can be said that the user is unlikely to feel mechanical resistance or the like in moving his/her finger.

Further, in the exemplary embodiment, when the switch 17 is turned on, the control unit 14 outputs a signal indicating the switch-on to the information processing unit 40. With this processing, the information processing unit 40 executes processing, that has been preset according to the switch-on signal, on contents that are displayed on the screen. On the other hand, when the switch 17 is turned off, the control unit 14 outputs a signal indicating the switch-off to the information processing unit 40. With this processing, the information processing unit 40 executes processing, that has been preset according to the switch-off signal, on the content displayed on the screen.

Figure 3:
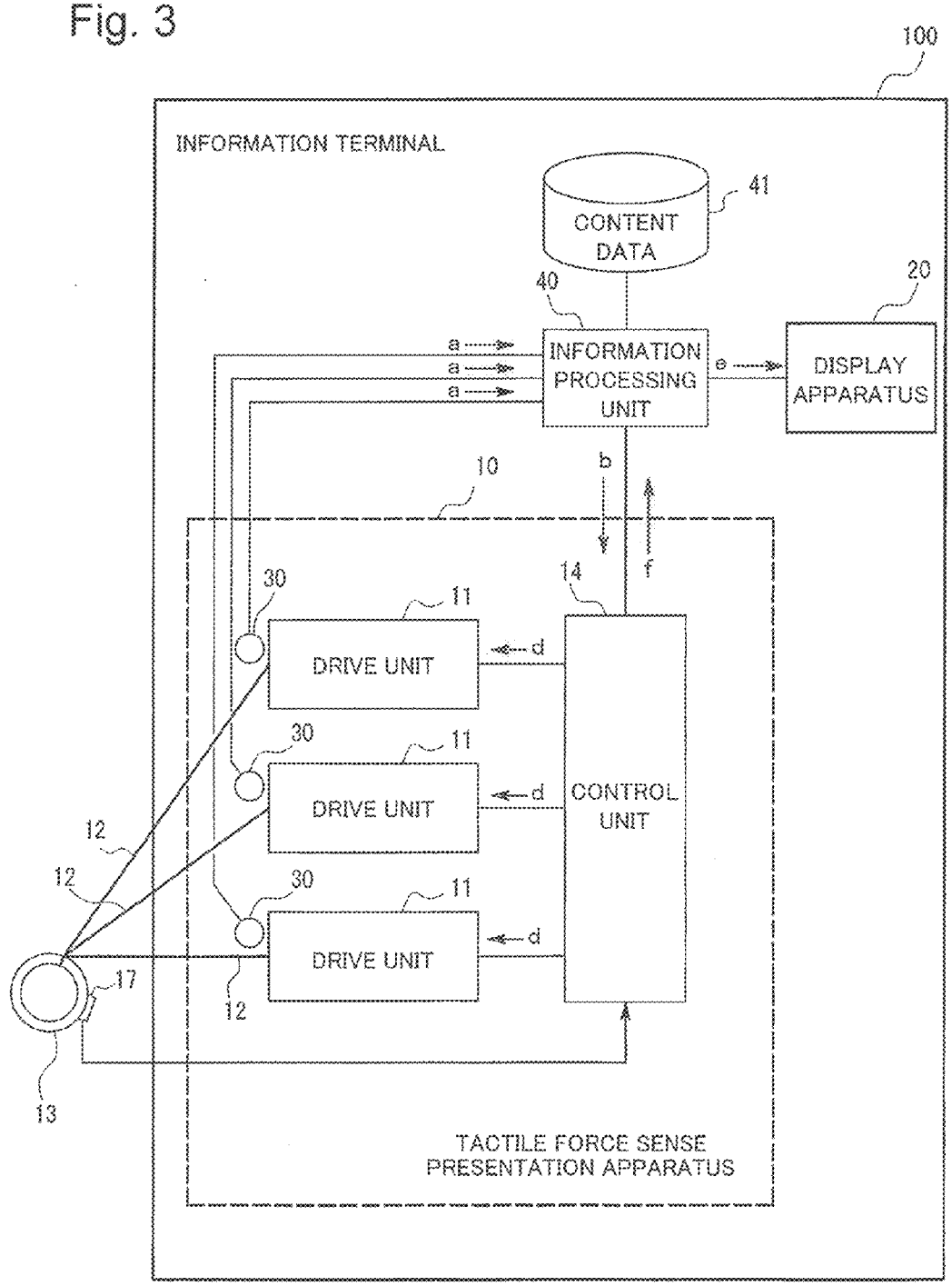
FIG. 3 is a block diagram illustrating a configuration of the information terminal in the exemplary embodiment of the present invention.

Next, referring to FIG. 3, data that are exchanged in the information terminal 100 will be described. FIG. 3 is a block diagram illustrating a configuration of the information terminal in the exemplary embodiment of the present invention.

As illustrated in FIG. 3, the information processing unit 40 is connected to the display apparatus 20, the position detection units 30, and the control unit 14. The control unit 14 is connected to the drive units (motors) 11.

In the configuration, when the user 200 moves his/her finger on which the fitting member 13 is attached, on the rear side of the information terminal 100, the respective position detection units 30 output position detection data "a" to the information processing unit 40. When the information processing unit 40 receives the respective position detection data "a", the information processing unit 40 identifies a position of the finger (fitting member 13) of the user 200 on the basis of the received position detection data "a".

When the information processing unit 40 identifies the position of the finger of the user 200, the information processing unit 40 changes the position of the user object 102 (refer to FIG. 1) in accordance with the identified position. Referring to content data 41, the information processing unit 40 then executes processing to associate the movement of the user object 102 with the movement of the virtual objects 103 and 104 in the content, and outputs display information of the content that reflects a result of the processing as display data "e" to the display apparatus 20.

Specific examples of the content data 41 include data used in an application program that provides a virtual space, such as a game program and a simulation program, and further include data of a Web site. The content data 41 may be stored in a storage apparatus installed in the information terminal 100 or another device (computer) connected to the information terminal 100 via the Internet.

At this time, the information processing unit 40 calculates force produced to the user object 102 in the virtual space and outputs data "b" identifying the calculated force (hereinafter, referred to as "presentation data 'b'") to the control unit 14. The calculated force is resilient force or the like produced to the user object 102, and is equivalent to the tactile force sense to be conveyed to the user.

When the control unit 14 receives the presentation data "b", the control unit 14 calculates tensile forces that the respective drive units 11 are required to output so that the tactile force sense identified by the presentation data "b" is conveyed to the user 200. The control unit 14 then generates control data "d" that make the respective drive units 11 produce the targeted tensile forces and outputs the generated control data "d" to the respective drive units 11.

Specifically, the control unit 14 generates pulse signals to drive the motors, which function as the drive units 11, using a power circuit (not illustrated) and outputs the generated pulse signals as the control data "d". With this processing, the respective drive units (motors) 11 wind the conveyance members 12 with the calculated tensile forces, and the tactile force sense identified by the presentation data "b" is provided to the finger of the user 200.

The control unit 14 also outputs a signal indicating a state of the switch 17 (hereinafter, referred to as "switch signal 'f'") to the information processing unit 40, in response to an operation of the switch 17 by the user. Specifically, when the switch 17 is turned on, the control unit 14 outputs a switch signal "f" set as a high level to the information processing unit 40. On the other hand, when the switch 17 is turned off, the control unit 14 outputs a switch signal "f" set as a low level to the information processing unit 40. When the switch signal "f" is output, the information processing unit 40 executes processing that has been preset, in accordance with the level of the switch signal "f".

[Operation of Apparatus]

Figure 4:
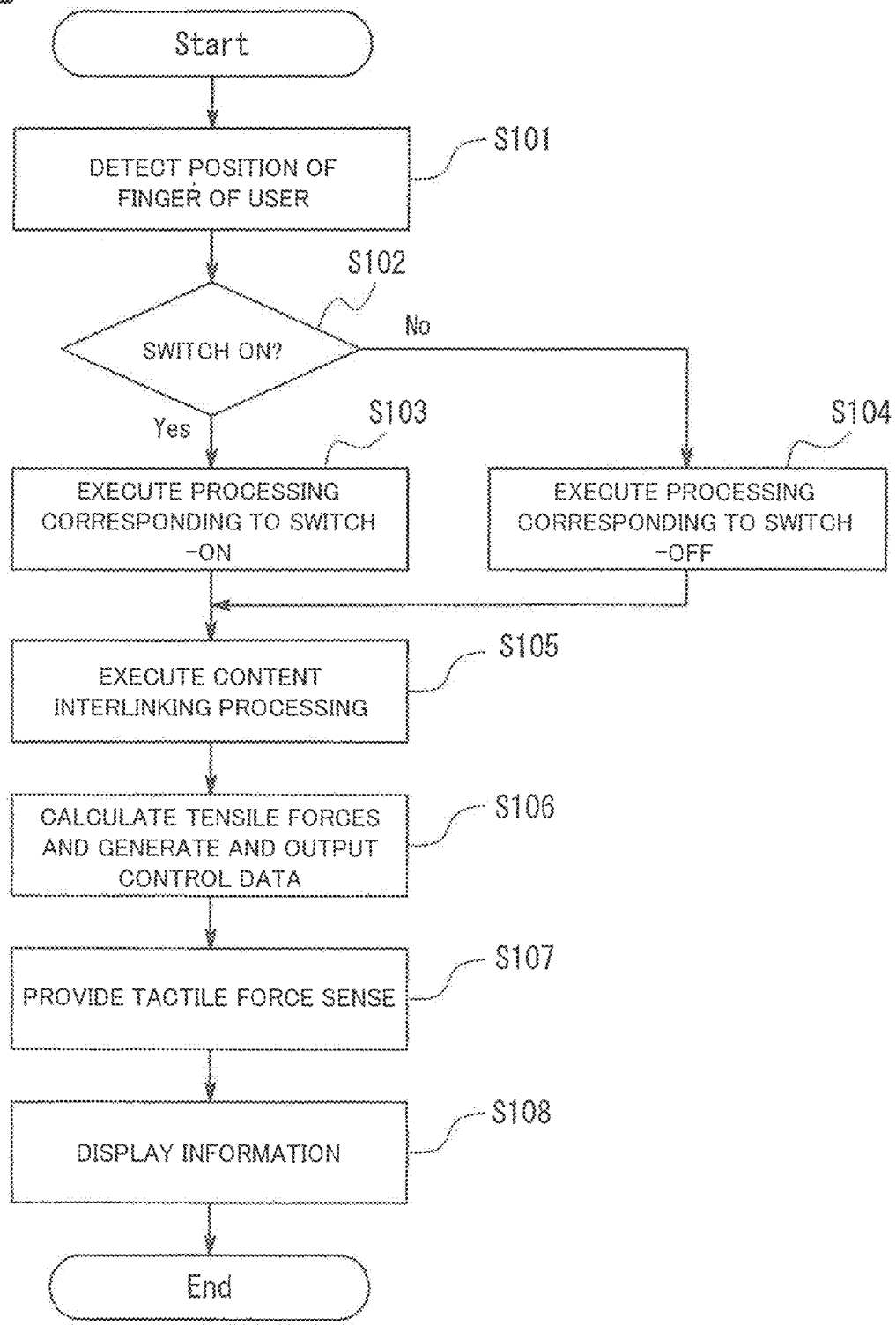
FIG. 4 is a flow chart illustrating an operation of an information terminal 100 in the exemplary embodiment of the present invention.

Next, operations of the information terminal 100 and the tactile force sense providing apparatus 10 in the exemplary embodiment of the present invention will be described referring to FIG. 4. FIG. 4 is a flow chart illustrating an operation of the information terminal 100 in the exemplary embodiment of the present invention. In the following description, FIGS. 1 to 3 are also taken into consideration appropriately. In the exemplary embodiment, a tactile force sense presentation method is performed through operating the tactile force sense providing apparatus 10. Thus, the following description of an operation of the tactile force sense providing apparatus 10 will also serve as a description of the tactile force sense presentation method in the exemplary embodiment.

First, the user 200 moves his/her finger in a space on the rear side of the information terminal 100 to manipulate contents displayed on the screen of the display apparatus 20. With this operation, as illustrated in FIG. 3, each position detection unit 30 outputs position detection data "a" to the information processing unit 40.

Next, as illustrated in FIG. 4, the information processing unit 40 calculates a length of each conveyance member 12 from the through hole 16 for the conveyance member 12 to the fitting member 13, on the basis of the output position detection data "a". The information processing unit 40, on the basis of the calculated lengths of the respective conveyance members 12, further identifies a position of the finger of the user 200 (S101). The information processing unit 40 changes the position of the user object 102 (refer to FIG. 1), in accordance with the identified position.

Next, on the basis of the switch signal "f" that the control unit 14 outputs, the information processing unit 40 determines whether or not the switch 17 has been turned on (step S102). When it is determined that the switch 17 has been turned on, the information processing unit 40 executes processing that has been preset according to the switch-on state (step S103). On the other hand, when it is decided that the switch 17 has been turned off, the information processing unit 40 executes processing that has been preset according to the switch-off state (step S104).

A condition other than whether the switch 17 has been turned on or off may be further added, as a condition to perform each of steps S103 and S104. For example, as a condition for executing step S103, a condition that the user object is in contact with or in proximity to a virtual object may be further added, in addition to the condition that the switch 17 has been turned on. As a condition to execute step S104, a condition that the switch 17 has been just switched from the on-state to the off-state may be further added, in addition to the condition that the switch 17 has been turned off. When such an additional condition is not satisfied, the information processing unit 40 does not execute step S103 or S104 and executes step S105.

Next, after executing step S104 or S103, the information processing unit 40 executes processing to associate the movement of the virtual objects 103 and 104 with the movement of the user object 102 (content interlinking processing), by referring to the content data 41 (step S105). In step S105, the information processing unit 40 outputs display information of the content that reflects a processing result of the content interlinking processing as display data "e" to the display apparatus 20. Further, in step S105, the information processing unit 40 calculates force produced to the user object 102 in the virtual space and outputs presentation data "b" identifying the calculated force to the control unit 14.

Next, when the control unit 14 receives the presentation data "b" from the information processing unit 40, the control unit 14 calculates tensile forces that the respective drive units 11 are to output for providing presentation force identified by the presentation data "b" (step S106). In step S106, the control unit 14 further generates control data "d" so that the calculated tensile forces are produced by the respective drive units 11, and outputs the generated control data "d" to the respective drive units 11.

When step S106 has been performed, in the tactile force sense providing apparatus 10, the motors included in the respective drive units 11 rotate in accordance with the output control data "d", to wind the conveyance members 12, and thereby provide a tactile force sense to a finger of the user 200 via the fitting member 13 (step S107). On the screen 101 of the display apparatus 20, the content, that the content interlinking processing has been executed, is displayed on the basis of the display data "e" that the information processing unit 40 has output in step S105 (step S108). Steps S107 and S108 may be executed at the same time.

In the exemplary embodiment, steps S101 to S108 are executed repeatedly. Thus, when the user 200 moves his/her finger from a position to another position, steps S101 to S108 are executed repeatedly during the period from the start to the end of the finger movement, which causes the user 200 to be able to receive provided tactile force senses continuously during the period.

Next, each of steps S101 to S106, which are illustrated in FIG. 4, will be described in further detail using FIGS. 5 to 8.

[Step S101]

Figure 5:
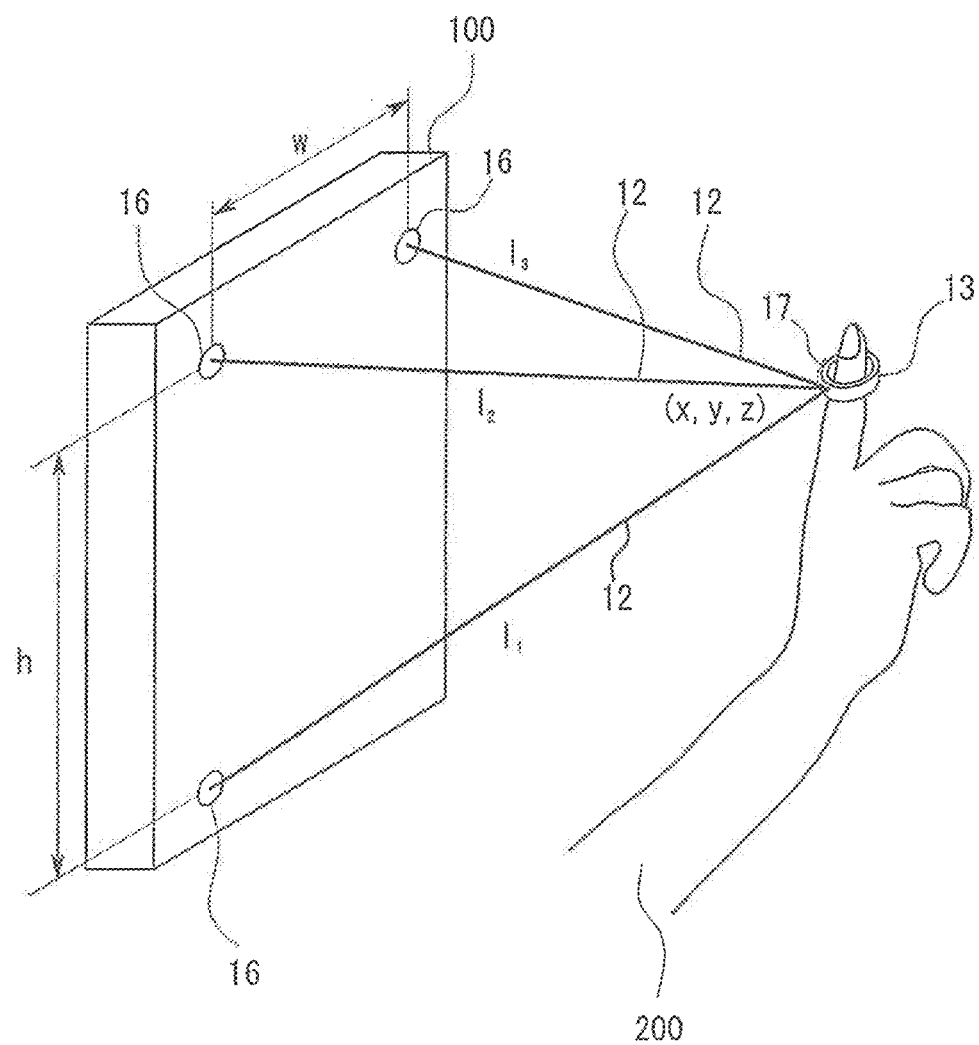
FIG. 5 is a diagram for a description of step S101 illustrated in FIG. 4.

First, by referring to FIG. 5, step S101 (finger position detection processing) illustrated in FIG. 4 will be described. FIG. 5 is a diagram for a description of step S101 illustrated in FIG. 4. In the finger position detection processing in step S101, the position of the fitting member 13 to which the tips of the conveyance members 12 are connected is, as described above, determined by the lengths of the conveyance members 12, on the rear side of the information terminal 100. The lengths of the conveyance members 12 are identified by the position detection units 30.

Specifically, it is assumed that, as illustrated in FIG. 5, the lengths of the respective conveyance members 12 from the through holes 16 therefor to the fitting member 13 are individually denoted by $l_1$, $l_2$, and $l_3$. It is also assumed the interval between through holes that are adjacent to each other in the horizontal direction on the screen are denotes by w, and the interval between through holes that are adjacent to each other in the vertical direction on the screen are denoted by and h. In this case, the information processing unit 40, by using $l_1$, $l_2$, $l_3$, w, and h, geometrically calculates the coordinates (x, y, z) of the fitting member 13.

[Steps S102 to S104]

Next, referring to FIG. 1, steps S102 to S104, which are illustrated in FIG. 4, will be described. In the following description, as illustrated in FIG. 1, a case of displaying molecular models as the virtual objects 103 and 104 in the content is used as an example.

For example, for the content illustrated in FIG. 1, it is assumed that processing that a virtual object sticks to the user object 102, has been set in the information processing unit 40, as processing performed when the switch 17 is turned on. It is also assumed that processing that a virtual object separates from the user object 102 has been set in the information processing unit 40, as processing performed when the switch 17 is turned off.

The user 200 moves a position of his/her finger, on which the fitting member 13 is attached, to make the user object 102 contact the virtual object 104 and, in this state, turns the switch 17 on. With this operation, the information processing unit 40 determines that the result in step S102 indicates "yes", and executes processing to make the virtual object 104 stick to the user object 102 in step S103. When the user moves the position of his/her finger, on which the fitting member 13 is attached, while keeping the switch 17 on, the information processing unit 40 also moves the virtual object 104 in accordance with the position of the finger in S105.

When the user turns the switch 17 off after the movement, the information processing unit 40 determines that the result in step S102 indicates "no", and, in step S104, executes processing to separate the virtual object 104 from the user object 102. When steps S102 to S104 are executed as described above, the user is able to move the virtual objects 103 and 104 freely by operating the switch 17.

In the above-described example, in addition to the condition that the switch 17 is on, the condition that the user object is in contact with or in proximity to a virtual object is further added as the condition to perform step S103. As the condition to perform step S104, the condition that the switch has been just switched from the on-state to the off-state is further added in addition to the condition that the switch is off.

In the exemplary embodiment, the processing that the information processing unit 40 executes in response to switch operations is not limited to the above-described examples, and details of the processing may be set in accordance with details of contents. Other processing that the information processing unit 40 executes in response to switch operations include grasping, throwing, receiving, rotating, opening, closing, or the like.

[Step S105]

Next, referring to FIG. 1, step S105 (content interlinking processing) illustrated in FIG. 4 will be described. In the content interlinking processing in step S105, as described above, the user object 102 moves in the virtual space in accordance with the actual movement of a finger of the user 200. Further, the movement of the virtual objects 103 and 104 is associated with the movement of the user object 102 in the virtual space.

Specifically, the information processing unit 40 moves the virtual object 103 or 104 in accordance with the movement of the user object 102 to achieve interaction between a virtual object in the virtual space and an object in the real space (a finger of the user 200). At this time, the information processing unit 40, by using a physical simulator in the virtual space, simulates changes in the positions of the user object 102 and the virtual object 103 or 104, and contact force between the user object 102 and the virtual object 103 or 104, when the user object 102 contacts the virtual object 103 or 104.

The information processing unit 40 calculates reaction forces produced to both the user object 102 and the virtual object 103 or 104 due to the contact on the basis of physical factors of the user object 102 and the virtual object 103 or 104 in the virtual space. The physical factors include mass, velocity, acceleration, a contact direction, a coefficient of restitution, or the like of each of the user object 102 and the virtual objects 103 and 104.

Among the calculated reaction forces, the reaction force exerted on the user object 102 by the virtual object 103 or 104 is equivalent to a tactile force sense to be provided to the user 200 (refer to the FIGS. 6 and 7 described below). When, it is assumed that the reaction force exerted on the user object 102 by the virtual object 103 is referred to as "presentation force F", the information processing unit 40 outputs presentation data "b" identifying the presentation force "F" to the control unit 14 to provide the presentation force "F". The information processing unit 40 also outputs data to display the user object 102 and the virtual objects 103 and 104 as display data "e", which is display information, to the display apparatus 20.

[Step S106]

Next, using FIGS. 6 and 7, step S106 (processing to calculate tensile forces and processing to generate control data) illustrated in FIG. 4 will be described.

Figure 6:
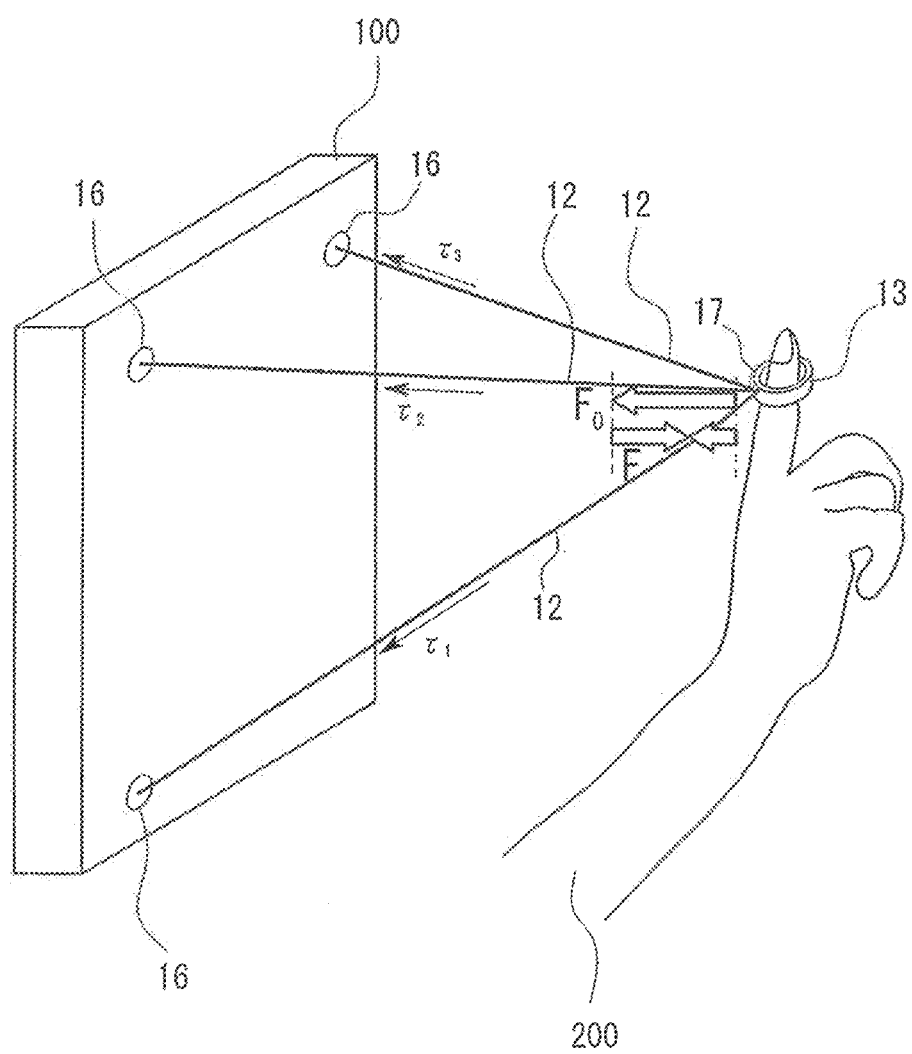
FIG. 6 is a diagram for a description of step S106 illustrated in FIG. 4.

FIG. 6 is a diagram for a description of step S106 illustrated in FIG. 4. As illustrated in FIG. 6, when it is assumed that tensile forces, in the respective conveyance members 12 required for providing the targeted presentation force "F", are individually denoted by $\tau_1$, $\tau_2$, and $\tau_3$, the presentation force "F" is basically equivalent to the resultant force of the tensile forces $\tau_1$, $\tau_2$, and $\tau_3$.

When the presentation force "F" is a force directed toward the information terminal 100 from the outside, the direction of the presentation force "F" is consistent to the direction of the resultant force of the tensile forces $\tau_1$ to $\tau_3$. However, when, as illustrated in FIG. 6, the presentation force "F" is a force in the direction away from the information terminal 100, the conveyance members 12 may become unable to provide a tactile force sense, because the conveyance members 12 are able to convey only a force in the pulling direction toward the information terminal 100 side since the conveyance members 12 are configured by string-like members.

Therefore, in the exemplary embodiment, the control unit 14, as described above, constantly provides a constant force to a finger of the user (fitting member 13) as an initial force "$F_0$" in advance, when no tactile force sense is provided. When the presentation force "F" is a force in the direction away from the information terminal 100, the control unit 14 provides a tactile force sense in the direction away from the information terminal 100, by relaxing the initial force "$F_0$".

In general, there is a phenomenon called adaptation which is a time characteristic of the tactile sense of a human being. Adaptation is a phenomenon that human sensitivity is reduced by continuously providing certain stimulus to a human being. That is, human skin can easily adapt to pressure, therefore, when a ring or a watch is attached, a feel of wearing the ring or watch is likely to be lost.

The above phenomenon also applies to gravity, and a human being does not aware the force of gravity usually. For example, although, when a train on which a person is on board accelerates or decelerates, a resultant force of inertial force and force of gravity is exerted on the person. However, the person on board the train does not feel the resultant force but feels only an inertial force in the direction of motion.

In the exemplary embodiment, by using the adaptability of a human being and increasing or decreasing the initial force "$F_0$", it is possible to present a tactile force sense in the direction toward the information terminal 100 and a tactile force sense in the direction away from the information terminal 100.

Subsequently, referring to FIG. 7, calculation processing of tensile forces $\tau_1$ to $\tau_3$, which are provided to the conveyance members 12, will be described specifically. Part (a) of FIG. 7 is a diagram for a description of the calculation processing of the tensile forces. Part (b) of FIG. 7 is a diagram illustrating coordinate axes used for the calculation processing of the tensile forces, respectively.

Figure 7:
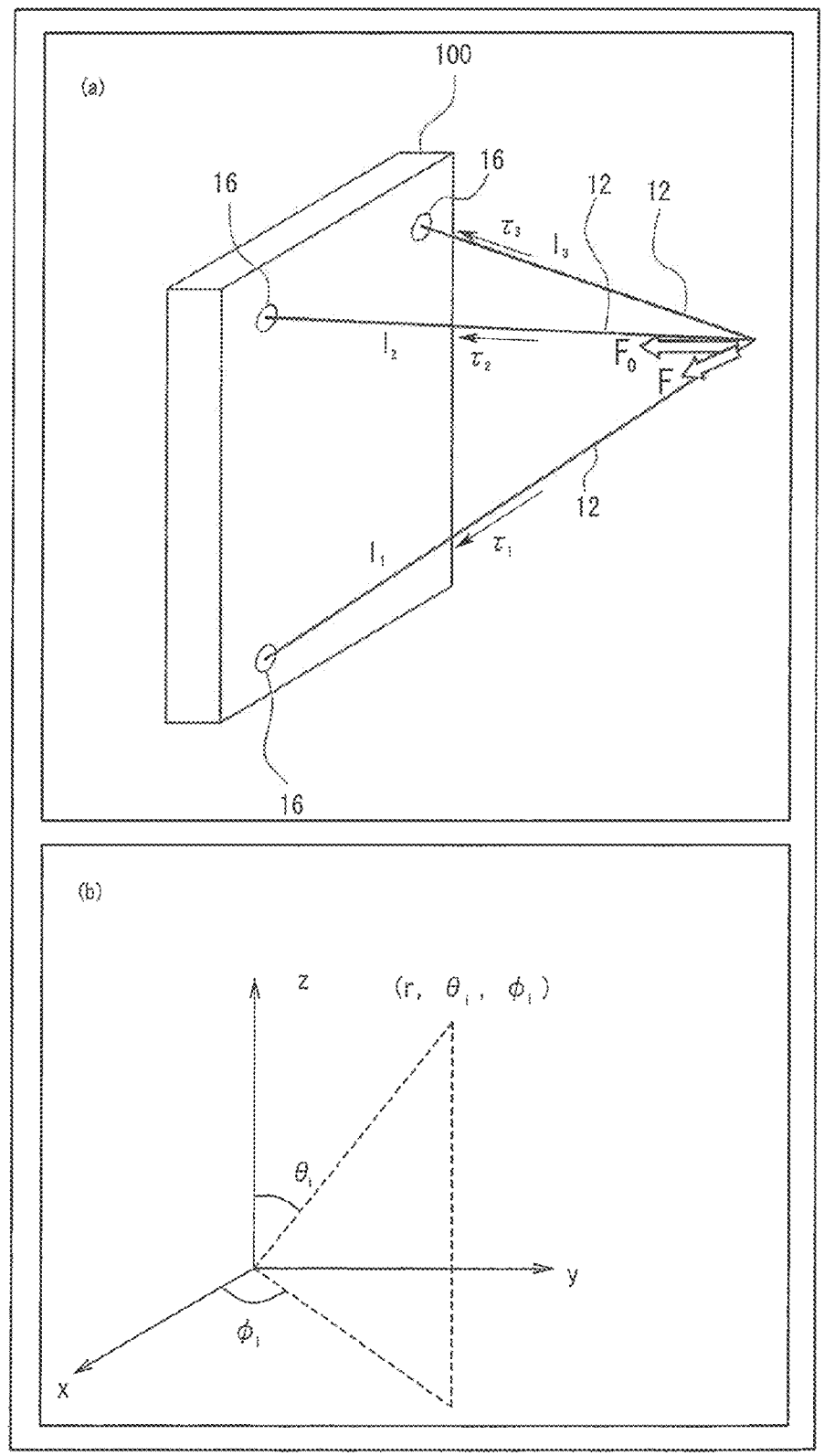
FIG. 7 Part (a) of FIG. 7 is a diagram for a description of calculation processing of tensile forces, and part (b) of FIG. 7 is a diagram illustrating coordinate axes used for the calculation processing of the tensile forces.

In part (a) and (b) in FIG. 7, the tensile forces $\tau_1$ to $\tau_3$ are tensile forces that are obtainable by excluding tensile forces required to produce the initial force "$F_0$", and are to be added to or subtracted from the initial force "$F_0$". In part (a) and (b) in FIG. 7, it is assumed that the origin of the coordinate axes is positioned at the tips of the respective conveyance members 12. Further, it is assumed that the x-axis, the y-axis, and the z-axis are axes parallel to the horizontal direction, the vertical direction, and the normal of the screen, respectively. In part (b) in FIG. 7, it is assumed that the coordinates of a unit vector r are denoted by $(r, \phi_i, \theta_i)$. In this case, the tensile forces $\tau_1$ to $\tau_3$ are required to satisfy a relation expressed by the equation 1 below to produce a targeted presentation force.

$$\sum_{i=1}^{3} \tau_i \Phi_i - F_0 = F \qquad \text{[Equation 1]}$$

In the above-described equation 1, the tensile forces $\tau_1$ to $\tau_3$ in the conveyance members 12 are scalar quantities, and the direction vector $\Phi_i$ of each of the tensile forces $\tau_1$ to $\tau_3$ is expressed by the equation 2.

$$\Phi_i = \begin{pmatrix} \sin \theta_i \cos \varphi_i \\ \sin \theta_i \sin \varphi_i \\ \cos \theta_i \end{pmatrix} \qquad \text{[Equation 2]}$$

The control unit 14 is capable of calculating the tensile forces $\tau_1$ to $\tau_3$ by using the above-described equations 1 and 2. As expressed in the above-described equation 1, a targeted presentation force "F" can be obtained by subtracting initial force "$F_0$" from tensile forces in the respective conveyance members 12. Thus, unless a presentation force "F" is a force that is in the direction away from the information terminal 100 (−z direction) and is larger than the initial force "$F_0$", the control unit 14 is able to provide a tactile force sense even in the direction away from the information terminal 100 (−z direction).

As a condition for the tensile forces in the respective conveyance members 12 to satisfy, the tensile forces are required to always take positive values because the tensile forces $\tau_1$, $\tau_2$, and $\tau_3$ can be provided only in the pulling direction. When it is assumed that a minimum value of the respective tensile forces is denoted by $\tau_{min}$, the equation 3 below is satisfied.

$$0 < \tau_{min} \leq \tau_i \qquad \text{[Equation 3]}$$

Figure 8:
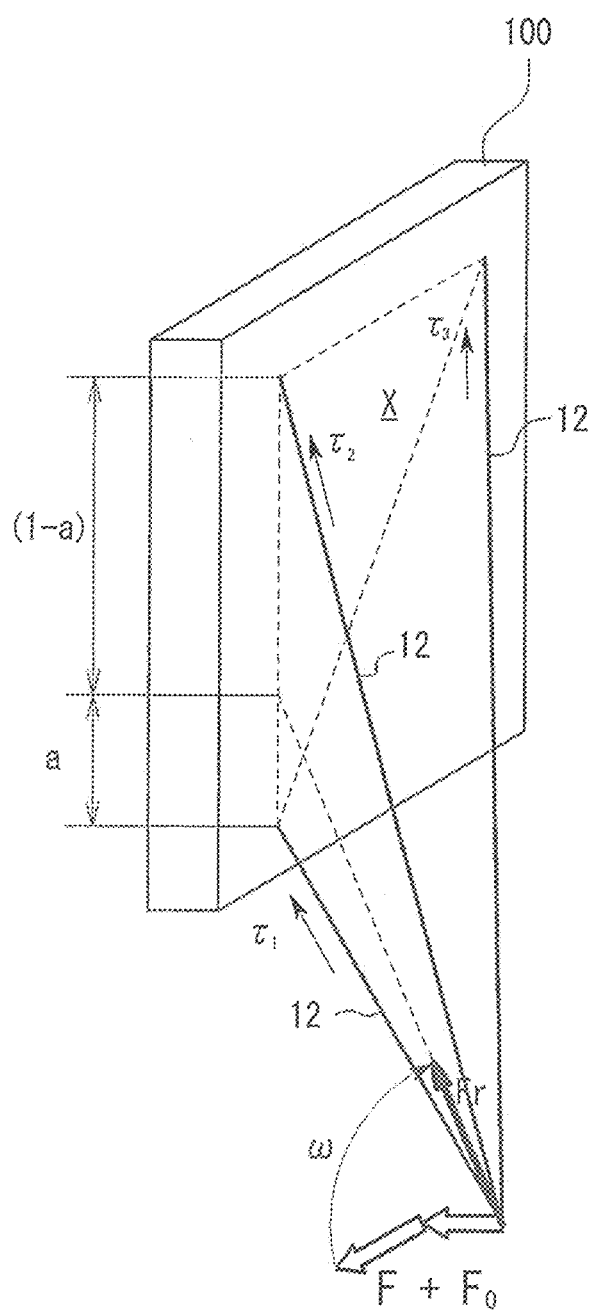
FIG. 8 is a diagram for a description of resetting processing of a presentation force.

Since the conveyance members 12 are able to convey only forces in pulling directions, there may be a situation in which resultant force of the tensile forces $\tau_1$, $\tau_2$, and $\tau_3$ cannot provide a tactile force sense required to be provided (refer to FIG. 8). Specifically, when the fitting member 13 is located at a position that, in the direction parallel to the normal of the screen (z-axis direction), does not overlap an area surrounded by straight lines each of which connects adjacent through holes 16 (refer to an area "X" in FIG. 8), there is a possibility that a targeted presentation force "F" cannot be calculated by use of the above-described equation 1. To handle such a case, in the exemplary embodiment, the control unit 14 resets the tactile force sense (presentation force "F") required to be provided. And the control unit 14 increases or decreases the initial force "$F_0$" so that the reset presentation force "Fr" is presented. The above-described resetting processing will be specifically described below.

FIG. 8 is a diagram for a description of the resetting processing of a presentation force. As illustrated in FIG. 8, for example, is assumed that a situation in which the fitting member 13 is located at a position (x, y, z) that does not overlap the area "X", which is surrounded by straight lines each of which connects adjacent through holes 16, in the z-axis direction.

In the case illustrated in FIG. 8, unless the element in the x-axis direction of the presentation force "F" takes a positive value, the presentation force "F" cannot be calculated by use of the above-described equations 1 and 2, regardless of how the tensile forces in the respective conveyance members 12 are set. On the other hand, even in such a condition, the user is able to move his/her finger to a position that overlaps the area "X" in the z-axis direction. Thus, in such a case, the control unit 14 resets the presentation force "Fr" so as to be able to calculate the tensile forces $\tau_1$, $\tau_2$, and $\tau_3$ by the above-described equations 1 and 2.

In the example in FIG. 8, a direction that the tensile forces $\tau_1$, $\tau_2$, and $\tau_3$ are expected to actually pull is the direction of the resultant force of the presentation force "F" and the initial force "$F_0$". However, the direction is not a direction that the resultant force, produced by the respective conveyance members 12, is able to generate a pulling force. Thus, the control unit 14 resets a force, that is closest to the resultant force of the presentation force "F" and the initial force "$F_0$", as a new presentation force "Fr".

In the example in FIG. 8, a presentation force "Fr" that is produced by the tensile forces $\tau_1$ and $\tau_2$ is close to the resultant force of the original presentation force "F" and the initial force "$F_0$". Thus, the control unit 14 resets the presentation force "Fr" as a new presentation force, by rotationally projecting the resultant force of the original presentation force "F" and the initial force "$F_0$" onto a plane formed by two conveyance members 12 that produce the tensile forces $\tau_1$ and $\tau_2$.

Specifically, a projection vector "V" onto a plane formed by two conveyance members 12 that produce the tensile forces $\tau_1$ and $\tau_2$ can be expressed by the equation 4 below. In the equation 4 below, the variable "a" indicates a position that minimizes the rotation angle ω when a rotational projection is applied, as illustrated in FIG. 8. That is, the variable "a" indicates, by ratio, the position of a point on the edge of the area "X" in the vertical direction on the screen (0<a<1). $\Phi_1$ is the direction vector of $\tau_1$ based on the corresponding through hole 16. $\Phi_2$ is the direction vector of $\tau_2$ based on the corresponding through hole 16. $\Phi_1$ and $\Phi_2$ can be obtained from the above-described equation 2.

$$V = a\tau_1\Phi_1 + (1-a)\tau_2\Phi_2 \quad \text{[Equation 4]}$$

Thus, the control unit 14, using the equation 5 below, calculates a projection vector that minimizes the inner product of the projection vector "V" and the resultant force of the original presentation force "F" and the initial force "$F_0$". The control unit 14 then applies the calculated projection vector to the equation 6 below to calculate the new presentation force "Fr". Subsequently, the control unit 14, using the new presentation force "Fr", calculates tensile forces $\tau_1$, $\tau_2$, and $\tau_3$ in the respective conveyance members 12. The control unit 15 generates control data "d" so that the calculated tensile forces are produced, and outputs the generated control data "d" to the respective drive units 11.

$$\min\{a\tau_1\Phi_1 + (1-a)\tau_2\Phi_2\} \cdot (F + F_0) \quad \text{[Equation 5]}$$

$$Fr = \frac{(F + F_0) \cdot V}{|V|^2} V - F_0 \quad \text{[Equation 6]}$$

(Variations of Exemplary Embodiment)

Although, in the above-described example, the number of conveyance members 12 is three, the number of conveyance members 12 is not limited to a specific number in the exemplary embodiment. The number of conveyance members 12 may be set within a range not upsizing the information terminal 100.

Although, in the above-described example, the motor is used as each drive unit 11, the drive units are not limited to motors in the exemplary embodiment. Each drive unit 11 may be an actuator that is capable of pulling a conveyance member, and as the drive unit 11, in addition to a motor, an artificial muscle actuator, a fibrous shape-memory-alloy actuator, or the like that performs tensile movement can be adoptable.

Although, in the above-described example, an encoder that determines a length of each conveyance member is used as each position detection unit 30, the position detection units 30 may be devices other than encoders in the exemplary embodiment. For example, as the position detection units 30, a camera that is disposed on the rear side of the information terminal may be used. In this case, the position of the fitting member 13 is detected optically. As the position detection units 30, a magnetic sensor that is disposed on the rear side of the information terminal may be used. In this case, position of the fitting member 13 can be detected by forming the fitting member 13 with a magnetic material.

Although, in the above-described example, the positions of the through holes 16, which are positions at which the conveyance members 12 start to be pulled, are arranged at the vertices of a right-angled triangle with a longitudinal direction length "h" and a lateral direction length "w", as illustrated in FIG. 5, the positions of the through holes 16 are not limited to specific positions in the exemplary embodiment. All through holes do not have to be arranged on an identical plane. The positions of the through holes 16 are appropriately set within a range allowed by the thickness of the information terminal 100.

Further, although, in the above-described example, the tactile force sense providing apparatus 10 is incorporated in the inside of the information terminal 100, the configuration of the exemplary embodiment is not limited to the example. In the exemplary embodiment, the tactile force sense providing apparatus 10 may be an apparatus that is attachable afterward to an existing information terminal as an attachment.

Although, in the above-described example, a tactile force sense is presented using the rear side of the information terminal 100 as an operation space, a space on the screen side of the information terminal 100 may be the operation space in the exemplary embodiment. However, in this case, the direction of an initial force "$F_0$" becomes the negative direction of the z-axis (refer to FIG. 6).

Although, in the above-described example, the tactile force sense providing apparatus is applied to a tablet-type information terminal, the configuration of the exemplary embodiment is not limited to the example. For example, the tactile force sense providing apparatus may be incorporated in a head-mounted display, which is mounted on the face of a user. In this case, the user is able to feel a sense of touch by moving his/her finger on which a fitting member is attached, in front of the head-mounted display, while watching a content displayed on a display panel inside the head-mounted display.

Figure 9:
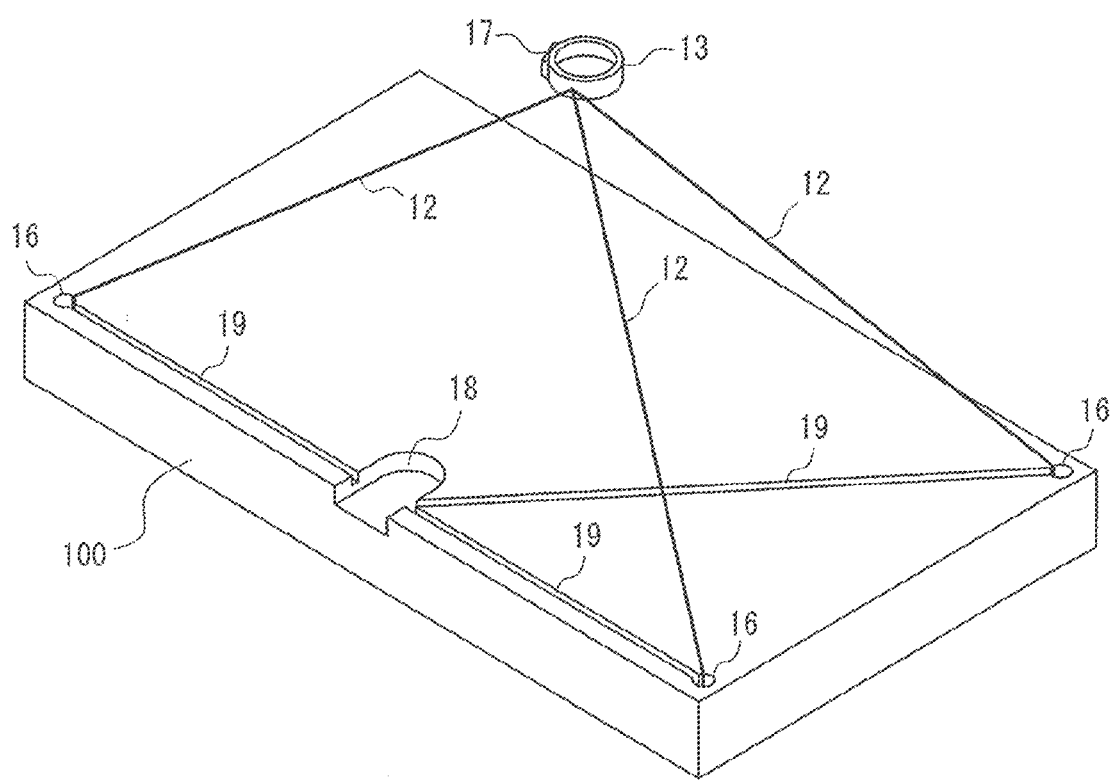
FIG. 9 is a perspective view illustrating another example of the information terminal in the exemplary embodiment of the present invention.

FIG. 9 is a perspective view illustrating another example of the information terminal in the exemplary embodiment of the present invention. As illustrated in FIG. 9, in the exemplary embodiment, a recess 18 to store the fitting member 13 and grooves 19 to store the conveyance members 12 may be formed on a casing constituting the information terminal 100. When embodied in the form illustrated in FIG. 9, it becomes easy for a user to carry the information terminal 100 including the tactile force sense providing apparatus.

Although, in the above-described example, a switch is used as the operation input unit 17, the configuration of the exemplary embodiment is not limited to the configuration. In the exemplary embodiment, for example, an acceleration sensor, a magnetic sensor, or a pressure sensor may be used as the operation input unit 17.

For example, it is assumed that an acceleration sensor is used as the operation input unit 17. In this case, when a user inputs an action of giving acceleration to the fitting member 13 as an operation, the operation input unit 17 outputs a signal identifying the acceleration produced by the operation to the control unit 14.

The control unit 14 is capable of identifying a direction and a quantity of the acceleration on the basis of the signal output from the operation input unit 17. And the control unit 14 outputs a signal that includes information indicating the identified direction and quantity of the acceleration, to the information processing unit 40. As a result, the information processing unit 40 is capable of calculating a product of the identified value of the acceleration and the mass of a virtual object and, on the basis of the calculated value and the identified direction of the acceleration, calculating an inertial force exerted on the user object in the virtual space accurately.

For another example, it is assumed that, as the operation input unit 17, a magnetic sensor is used. In this case, another magnetic sensor is mounted on the casing 51 or the like of the information terminal 100. When a user inputs, as an operation, an action of moving the direction of his/her finger on which the fitting member 13 is attached, the operation input unit 17 outputs a signal that identifies a change in magnetic force between the operation input unit 17 itself (magnetic sensor) and the magnetic sensor mounted on the casing 51 or the like to the control unit 14.

On the basis of the signal output from the operation input unit 17, the control unit 14 is capable of outputting a signal that identifies a direction of the finger on which the fitting member 13 is attached, to the information processing unit 40. As a result, the information processing unit 40 is capable of identifying a direction of the user object using the output signal. And, the information processing unit 40 is able to calculate forces exerted on the user object and a virtual object, by taking into consideration the identified direction of the user object.

For another example, it is assumed that, as the operation input unit 17, a pressure sensor is used. In this case, the pressure sensor is mounted at the same position as the switch illustrated in FIGS. 1 and 2. When the pressure sensor is pressed by a finger other than the finger on which the fitting member 13 is attached, the pressure sensor outputs a signal of which level changes in accordance with the magnitude of pressing force, to the information processing unit 40.

On the basis of the signal output from the operation input unit 17, the control unit 14 is capable of identifying pressure caused by the pressing force and outputting a signal that includes information indicating the identified pressure to the information processing unit 40. As a result, since the information processing unit 40 is capable of calculating a force that the user object provides to a virtual object more accurately, the user becomes able to press the virtual object slowly with a larger force, or the like.

(Application Examples)

In addition, although, in FIG. 1, an example in which molecular models are displayed as virtual objects is illustrated as an example of a content in which a tactile force sense is presented, there is no limitation to a content in the exemplary embodiment. In the following, cases in which other contents are displayed on the screen of the information terminal (refer to FIG. 1) will be described by referring to FIGS. 10 to 13. FIGS. 10 to 13 individually illustrate examples of contents displayed on the screen of the information terminal in the exemplary embodiment of the present invention.

Figure 10:
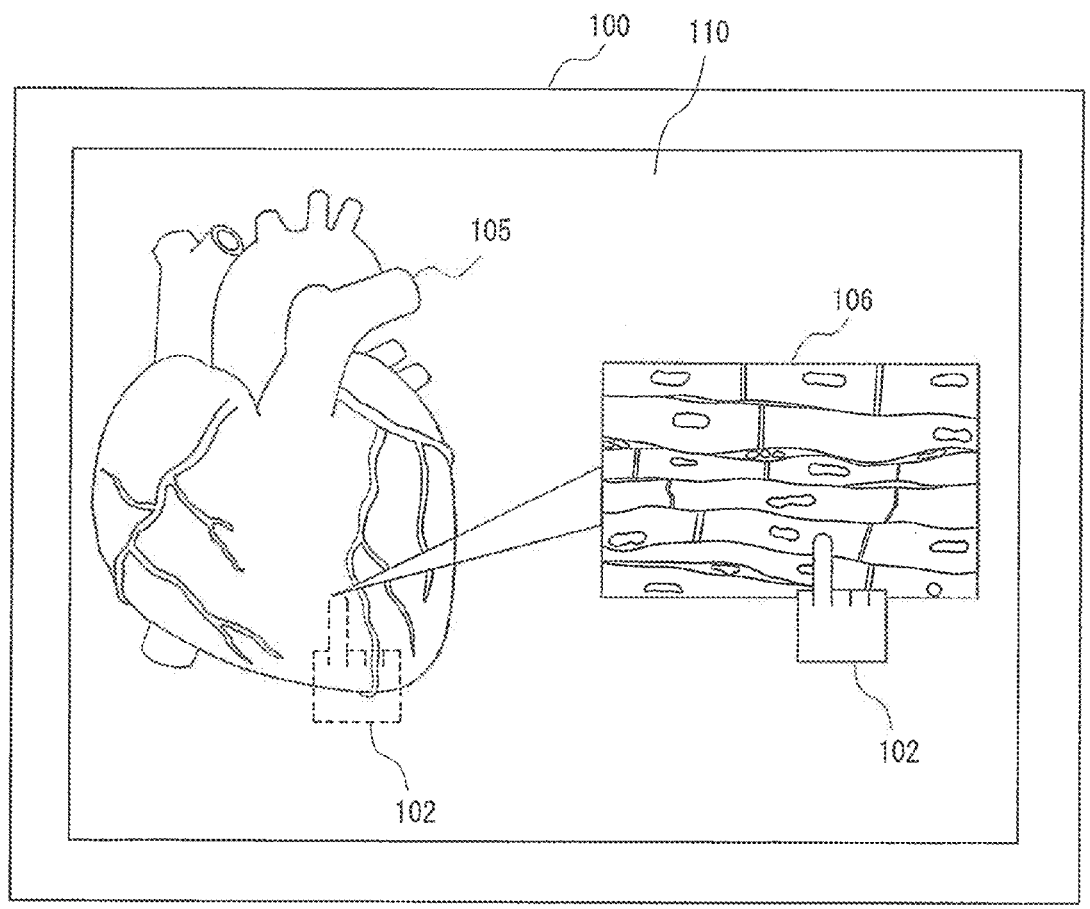
FIG. 10 illustrates an example of a content displayed on a screen of the information terminal in the exemplary embodiment of the present invention.

FIG. 10 illustrates a case that a content displayed on the screen of the information terminal is a human body model. In the example in FIG. 10, a three-dimensional model of a human heart (hereinafter, referred to as "heart model") 105 is displayed on the screen 101 of the information terminal 100 as a virtual object. The heart model 105 moves as like a real heart.

Thus, when, as illustrated in FIG. 10, a user moves his/her finger on which the fitting member 13 (not illustrated in FIG. 10) is attached to make the user object 102 come in contact with the heart model 105, a tactile force sense that expresses a heartbeat is presented to the user.

In the example in FIG. 10, when the user turns the switch 17 (refer to FIGS. 2 and 3) on in a state that the user object 102 and with the heart model 105 are in contact with each other, the information processing unit 40 (refer to FIGS. 2 and 3) displays an enlarged view 106 of the contact portion. In the enlarged view 106, cardiac muscle cells are displayed, and, when the user moves the user object 102 to the enlarged view 106, a tactile force sense that expresses movement of the cardiac muscle cells is provided to the user.

As described above, by using the tactile force sense providing apparatus in the exemplary embodiment, the user is able to feel a heartbeat that only a medical doctor can feel, when the content illustrated in FIG. 10 is displayed.

Figure 11:
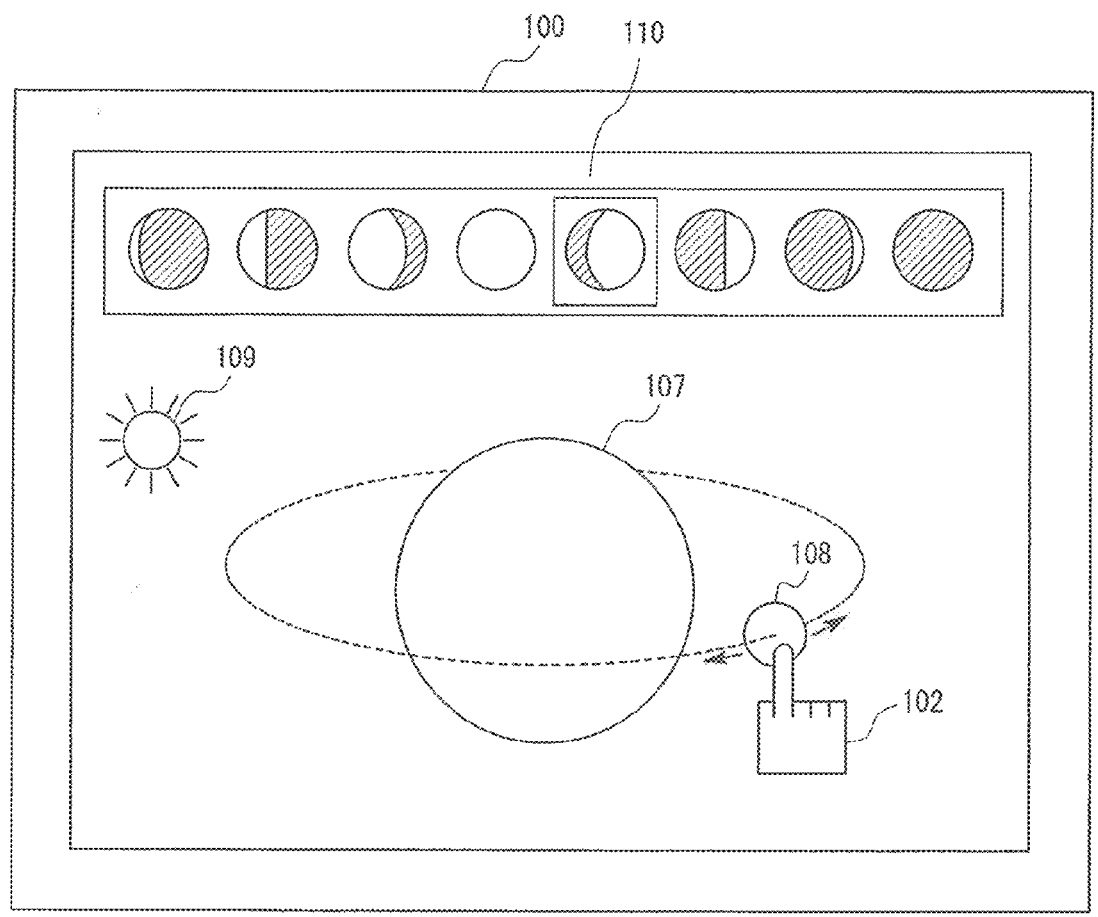
FIG. 11 illustrates an example of a content displayed on the screen of the information terminal in the exemplary embodiment of the present invention.

FIG. 11 illustrates a case that a content displayed on the screen of the information terminal is astronomical object models. In the example in FIG. 11, an astronomical object model imitating the earth (hereinafter, referred to as "earth model") 107, an astronomical object model imitating the moon (hereinafter, referred to as "moon model") 108, and an astronomical object model imitating the sun (hereinafter, referred to as "sun model") 109 are displayed on the screen 101 of the information terminal 100 as virtual objects. The moon model 108 is configured to be able to move around the earth model 107 on an orbit, as with reality.

Thus, when, as illustrated in FIG. 11, the user moves his/her finger on which the fitting member 13 (not illustrated in FIG. 11) is attached to make the user object 102 come into contact with the moon model 108, a tactile force sense that expresses contact with the moon is presented to the user. In the example in FIG. 11, when the user turns the switch 17 (refer to FIGS. 2 and 3) on in a state that the moon model 108 and the user object 102 are in contact with each other, the information processing unit 40 (refer to FIGS. 2 and 3) executes processing to make the moon model 108 stick to the user object 102.

Thus, when, the user moves the user object 102 along the orbit around the earth model 107, by moving the position of his/her finger on which the fitting member 13 is attached, while keeping the switch 17 on, the user is also able to move the moon model 108 along the orbit together.

At this time, states of the moon model 108 when viewed from an arbitrary position on the earth model 107 are displayed in a space 110 at the top portion of the screen. Specifically, typical examples of the waxing and waning of the moon is displayed in the space 110 at the top portion of the screen, and an example corresponding to a present state of the moon model 108 is displayed in such a way surrounded by a square.

As described above, by using the tactile force sense providing apparatus in the exemplary embodiment, the user is able to feel the existence of astronomical objects that the user is unable to feel by nature, when the content illustrated in FIG. 11 is displayed.

Figure 12:
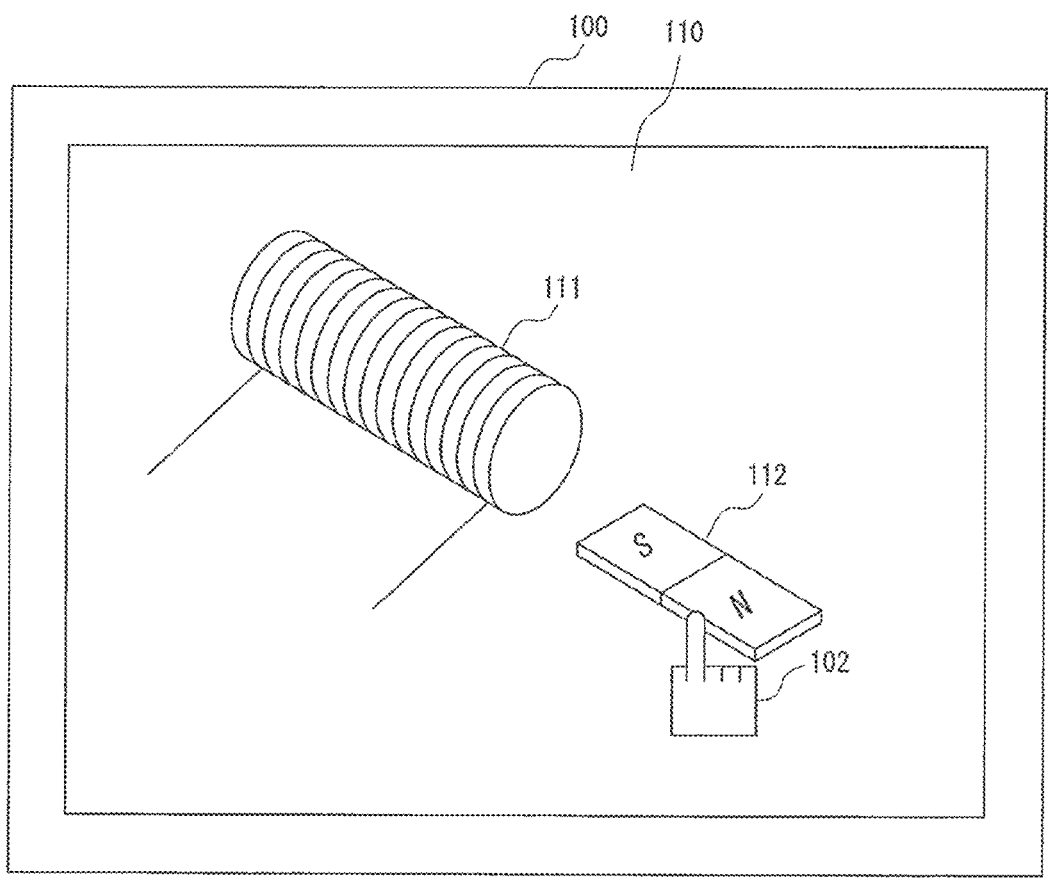
FIG. 12 illustrates an example of a content displayed on the screen of the information terminal in the exemplary embodiment of the present invention.
Figure 13:
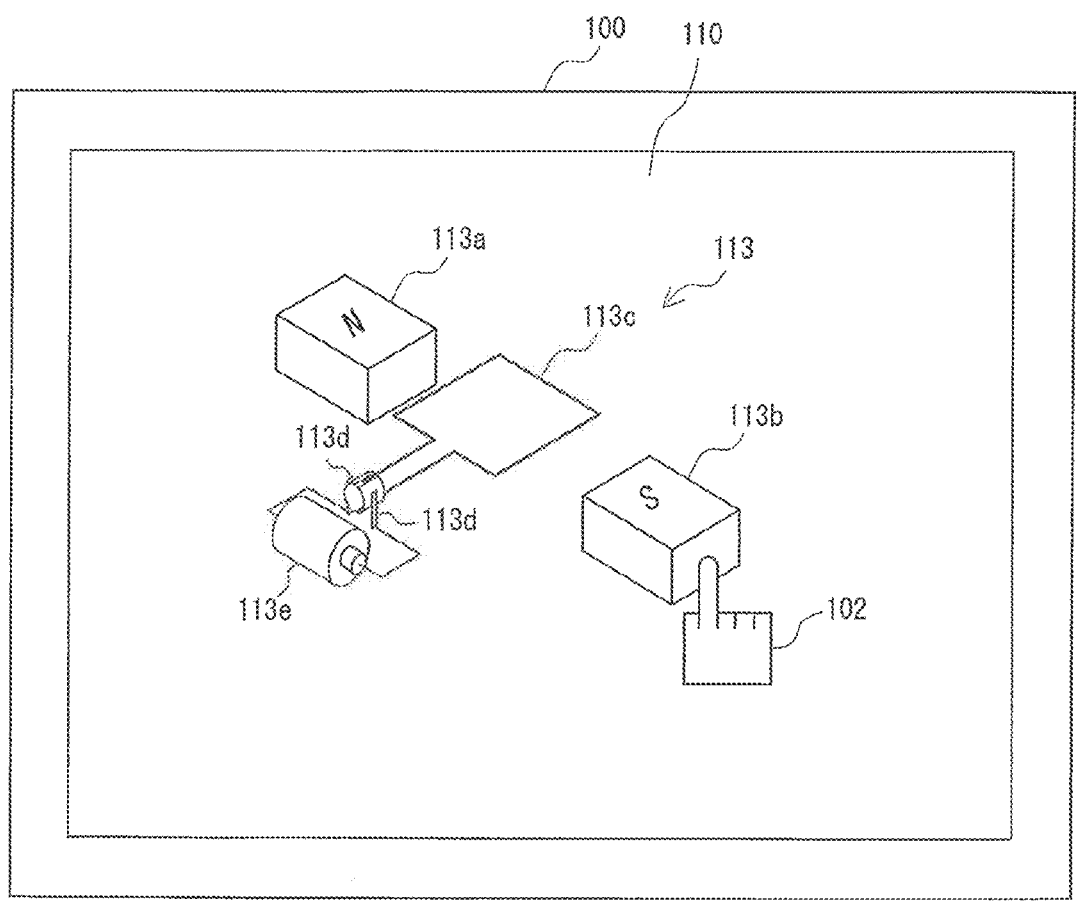
FIG. 13 illustrates an example of a content displayed on the screen of the information terminal in the exemplary embodiment of the present invention.

FIGS. 12 and 13 illustrate cases in which contents displayed on the screen of the information terminal are scientific experiment models. Specifically, in the example in FIG. 12, the experiment model is composed of an electromagnet and a permanent magnet. On the screen 101 of the information terminal 100, a three-dimensional model of the electromagnet (hereinafter, referred to as "electromagnet model") 111 and a three-dimensional model of the permanent magnet (hereinafter, referred to as "permanent magnet model") 112 are displayed as virtual objects.

In the example in FIG. 12, when a user turns the switch 17 (refer to FIGS. 2 and 3) on in a state that the permanent magnet model 112 and the user object 102 are in contact with each other, the information processing unit 40 (refer to FIGS. 2 and 3) executes processing to make the permanent magnet model 112 stick to the user object 102.

Thus, when the user moves the position of his/her finger on which the fitting member 13 is attached to make the user object 102 come close to the electromagnet model 111 while keeping the switch 17 on, the user is able to make the permanent magnet model 112 come close to the electromagnet model 111. In this case, a tactile force sense expressing magnetic force that the permanent magnet model 112 receives from the electromagnet 111 is provided to the user.

As described above, by using the tactile force sense providing apparatus in the exemplary embodiment when the content illustrated in FIG. 12 is displayed, the user is able to feel magnetic force in the virtual space. By changing, the number of turns of a coil, the value of a current flowing through the coil, and the value of voltage applied across the coil of the electromagnet model 111 in the content, the user is also able to feel changes in the magnetic force caused by changes in the conditions.

In the example in FIG. 13, the experiment model is a motor, and a three-dimensional model of the motor (hereinafter, referred to as "motor model") 113 is displayed on the screen 101 of the information terminal 100 as a virtual object. The motor model 113 is configured with a first three-dimensional permanent magnet model 113a, a second three-dimensional permanent magnet model 113b, a three-dimensional coil model 113c, a pair of three-dimensional brush models 113d, and a three-dimensional battery model 113e.

Further, in the example in FIG. 13, when the user turns the switch 17 (refer to FIGS. 2 and 3) on in a state that any one of the three-dimensional models and the user object 102 are in contact with each other, the information processing unit 40 (refer to FIGS. 2 and 3) executes processing to make the three-dimensional model in contact stick to the user object 102.

Thus, for example, when the user turns the switch 17 on with the user object 102 being kept in contact with the three-dimensional coil model 113c, a tactile force sense expressing torque of the coil is presented to the user.

When the user turns the switch 17 on with the user object 102 being kept in contact with the second three-dimensional permanent magnet model 113b, the user is able to keep the second three-dimensional permanent magnet model 113b away from the three-dimensional coil model 113c. Or the user is able to let the second three-dimensional permanent magnet model 113b come close to the three-dimensional coil model 113c. In this case, the user is able to confirm an influence that the distance between the coil and the permanent magnet gives to rotation of the coil.

As described above, by using the tactile force sense providing apparatus in the exemplary embodiment, the user is able to understand not only the structure of the motor but also roles of respective components in the virtual space, when the content illustrated in FIG. 13 are displayed.

[Program]

A program in the exemplary embodiment may be a program that arrows a computer to execute step S106 illustrated in FIG. 4. Installing the program into the computer and executing the program make it possible to realize the tactile force sense providing apparatus 10 and the tactile force sense presentation method in the exemplary embodiment. In this case, a CPU (Central Processing Unit) of the computer functions as the control unit 14 to perform the processing.

The computer that is capable of realizing the tactile force sense providing apparatus 10 is not particularly limited to a specific computer, and may be the above-described microcomputer or a general purpose personal computer. Further, the computer that is capable of realizing the tactile force sense providing apparatus 10 may also be a computer that is included in a mobile phone, a smart phone, or a tablet-type information terminal.

The program in the exemplary embodiment may be provided recorded in a computer-readable recording medium or transmitted via the Internet. Specific examples of such recording media include a general purpose semiconductor storage device, such as a CF (Compact Flash) and a SD (Secure Digital), a magnetic storage medium, such as a Flexible Disk, and an optical storage medium, such as a CD-ROM (Compact Disk Read Only Memory).

[Advantageous Effect of Exemplary Embodiment]

As described thus far, in the exemplary embodiment, when a user moves his/her finger for an operation in a space on the rear side of the information terminal, while watching a content on the screen from the front side of the information terminal, the user is able to feel a tactile force sense in accordance with details of the content. Thus, by using the exemplary embodiment, it is possible to secure a sufficiently large operation area and provide a three-dimensional tactile force sense in a wide range that is not only wide in two-dimensions but also wide in depth directions. Further, when the user inputs an operation via the operation input unit that is mounted on the fitting member, a signal is output to the information processing unit 40 in response to the input, which improves the degree of freedom of actions taken by the user.

In the exemplary embodiment, a tactile force sense is produced by taking a perception characteristic of a human into consideration. Thus, the produced tactile force sense becomes a sense that does not cause a strange feeling to a user. Further, securing sufficient lengths of the conveyance members enables the user to move his/her finger largely, and, in this respect, the tactile force sense also becomes a sense that does not cause a strange feeling to the user.

It is possible, in particular, to downsize and reduce weight of the apparatus, since it is possible to prevent that the tactile force sense providing apparatus becomes complicated string-like members as conveyance members. Further, since it is not required to arrange motors or the like in the operation space, it becomes possible to apply the tactile force sense providing apparatus to a portable information terminal.

All or part of the exemplary embodiment described above may be described as in the following Supplemental Notes 1 to 14, but the present invention is not limited thereto.

(Supplemental Note 1)

A tactile force sense providing apparatus to provide a tactile force sense to a user in accordance with a content displayed on a screen, including:

a fitting member that is formed so as to be attached on a portion of the user that receives the tactile force sense to be provided, and includes an operation input unit to input an operation performed by the user;

a conveyance member that extends from the apparatus to the fitting member and conveys a force in a pulling direction to the user via the fitting member;

a drive unit that produces the force in the pulling direction and provides the produced force to the conveyance member; and a control unit that is configured to:

produce the force in the pulling direction of a preset magnitude to the drive unit as an initial force in advance;

increase or decrease the initial force so that the tactile force sense required to be provided is provided to the user via the fitting member on providing the tactile force sense, and,
when the user inputs an operation via the operation input unit, further output a signal in accordance with the input operation.

(Supplemental Note 2)

The tactile force sense providing apparatus according to Supplemental Note 1, including:
a plurality of the conveyance members; and
a plurality of the drive units each of which corresponds to one of the plurality of the conveyance members, wherein
each of the plurality of the conveyance members is string-like member that extends from different positions of the own apparatus to the fitting member attached on the user,
each of the plurality of the drive units, by winding in the corresponding conveyance member, provides the force in the pulling direction to the corresponding conveyance member, and
the tactile force sense is provided by a resultant force of the forces in the pulling directions that are provided to the conveyance members by respective ones of the plurality of drive units.

(Supplemental Note 3)

The tactile force sense providing apparatus according to Supplemental Note 2, wherein
at least one of the plurality of the conveyance members functions as wiring connecting the operation input unit to the control unit.

(Supplemental Note 4)

The tactile force sense providing apparatus according to Supplemental Note 2 or 3, wherein
three or more string-like members are included.

(Supplemental Note 5)

The tactile force sense providing apparatus according to any one of Supplemental Note 1,
wherein, when a condition, in which the tactile force sense required to be provided is not able to be produced by the resultant force in the pulling direction, is caused, the control unit resets the tactile force sense required to be provided and increases or decreases the initial force so that the reset tactile force sense is provided.

(Supplemental Note 6)

The tactile force sense providing apparatus according to any one of Supplemental Note 1, wherein
the operation input unit is any one of a switch, an acceleration sensor, a magnetic sensor, and a pressure sensor.

(Supplemental Note 7)

An information terminal that is capable of providing a tactile force sense to a user in accordance with details of a content displayed on a screen, including:
a display apparatus that displays the content on the screen;
a position detection unit that detects a position of a portion of the user that receives the tactile force sense to be provided;
an information processing unit that changes details of the content in accordance with the detected position and, on the basis of the changed details of the content, calculates a tactile force sense required to be provided; and
a tactile force sense providing apparatus,
the tactile force sense providing apparatus including:
a fitting member that is formed so as to be attached on a portion of the user that receives the tactile force sense to be provided and includes an operation input unit to input an operation performed by the user;
a conveyance member that extends from the information terminal to the fitting member and conveys a force in a pulling direction to the user via the fitting member;
a drive unit that produces the force in the pulling direction and providing the produced force to the conveyance member; and
a control unit that is configured to:
produce the force in the pulling direction of a preset magnitude as an initial force to the drive unit in advance,
increase or decrease the initial force so that the calculated tactile force sense is provided to the user via the fitting member on providing the tactile force sense calculated by the information processing unit, and
when the user inputs an operation via the operation input unit, further output a signal in accordance with the input operation to the information processing unit, and,
the information processing unit changing details of the content in accordance with details of the signal, when the control unit outputs the signal.

(Supplemental Note 8)

The information terminal according to Supplemental Note 7, further including:
a plurality of the conveyance members; and
a plurality of the drive units each of which corresponds to one of the plurality of the conveyance members, wherein
each of the plurality of the conveyance members is string-like member that extends from different positions of the information terminal to the fitting member fitted on the user,
each of the plurality of the drive units, by widing in the corresponding conveyance member, provides the force in the pulling direction to the corresponding conveyance member, and
the tactile force sense is provided by a resultant force of the forces in the pulling directions that are provided to the conveyance members by respective ones of the plurality of the drive units.

(Supplemental Note 9)

The information terminal according to Supplemental Note 8, wherein
at least ones of the plurality of the conveyance members functions as wiring connecting the operation input unit to the control unit.

(Supplemental Note 10)

The information terminal according to Supplemental Note 8, wherein
three or more string-like members are included.

(Supplemental Note 11)

The information terminal according to any one of Supplemental Note 7, wherein,
when a condition, in which the tactile force sense required to be provided is not able to be produced by the resultant force in the pulling direction, is caused, the control unit resets the tactile force sense required to be provided and increases or decreases the initial force so that the reset tactile force sense is provided.

(Supplemental Note 12)

The information terminal according to any one of Supplemental Note 7, wherein the operation input unit is any one of a switch, an acceleration sensor, a magnetic sensor, and a pressure sensor.

(Supplemental Note 13)

A tactile force sense providing method to provide a tactile force sense to a user in accordance with details of a content displayed on a screen, the method including by using an apparatus including a fitting member that is formed so as to be attached on a portion of the user that receives the tactile force sense to be provided and includes an operation input unit to input an operation performed by the user, a conveyance member that extends to the fitting member and conveys a force in a pulling direction to the user, and a drive unit that produces the force in the pulling direction and provides the produced force to the conveyance member:

(a) a step of producing a force in a pulling direction of a preset magnitude to the drive unit as an initial force in advance;

(b) a step of increasing or decreasing the initial force so that the tactile force sense to be provided is provided to the user via the fitting member on providing the tactile force sense; and (c) a step of, when the user inputs an operation via the operation input unit, outputting a signal in accordance with the input operation.

(Supplemental Note 14)

A computer-readable recording medium storing a program including instructions for a computer, the computer being included in an apparatus to provide a tactile force sense to a user in accordance with details of a content displayed on a screen, the apparatus including a fitting member that is formed so as to be attached on a portion of the user that receives the tactile force sense to be provided and includes an operation input unit to input an operation performed by the user, a conveyance member that extends to the fitting member and conveys a force in a pulling direction to the user, a drive unit that produces the force in the pulling direction and provides the produced force to the conveyance member, and the computer, the program allowing the computer to execute:

(a) a step of producing a force in a pulling direction of a preset magnitude to the drive unit as an initial force in advance;

(b) a step of increasing or decreasing the initial force so that the tactile force sense to be provided is provided to the user via the fitting member on providing the tactile force sense; and (c) a step of, when the user inputs an operation via the operation input unit, outputting a signal in accordance with the input operation.

The present invention was described above by use of an exemplary embodiment thereof, but the present invention is not limited to the above exemplary embodiment. Various modifications that could be understood by a person skilled in the art may be applied to the configurations and details of the present invention within the scope of the present invention.

This application claims priority based on Japanese Patent Application No. 2013-199728, filed on Sep. 26, 2013, the entire disclosure of which is incorporated herein by reference.

INDUSTRIAL APPLICABILITY

As described above, according to the present invention, it is possible to achieve an improvement in the degree of freedom of actions taken by the user in a tactile force sense providing apparatus while downsizing the apparatus. The present invention is useful in various fields in which presentation of a tactile force sense is required, such as computer interfaces, various types of simulation, and games.

REFERENCE SIGNS LIST

10 Tactile force sense providing apparatus
11 Drive unit
12 Conveyance member
13 Fitting member
14 Control unit
15 Pulley
16 Through hole
17 Operation input unit
18 Recess for switch storage
19 Recess for conveyance member storage
20 Display apparatus
30 Position detection unit
31 Virtual touch panel
32 Virtual keyboard
40 Information processing unit
50 Cover
51 Casing
60 Head-mounted display
70 Camera
71 Advertisement
100 Information terminal
101 Screen
102 User object
103, 104 Virtual object (molecular model)
105 Virtual object (three-dimensional heart model)
106 Enlarged view
107 Virtual object (astronomical object model imitating the earth)
108 Virtual object (astronomical object model imitating the moon)
109 Virtual object (astronomical object model imitating the sun)
110 Space to display examples of the waxing and waning of the moon
111 Virtual object (three-dimensional electromagnet model)
112 Virtual object (three-dimensional permanent magnet model)
113 Virtual object (three-dimensional motor model)
113a, 113b Virtual object (three-dimensional permanent magnet model)
113c Virtual object (three-dimensional coil model)
113d Virtual object (a pair of three-dimensional brush models)
113e Virtual object (three-dimensional battery model)
200 User
a Position detection data
b Presentation data
d Control data
e Display data

The invention claimed is:

1. A tactile force sense providing apparatus to provide a tactile force sense to a user in accordance with a content displayed on a screen, comprising:
a fitting member that is formed so as to be attached on a portion of the user that receives the tactile force sense to be provided, and comprises an operation input unit that is configured to input an operation performed by the user;

a conveyance member that extends from the apparatus to the fitting member and is configured to convey a force in a pulling direction to the user via the fitting member;

a drive unit that is configured to produce the force in the pulling direction and to provide the produced force to the conveyance member; and a control unit that is configured to:
produce the force in the pulling direction of a preset magnitude to the drive unit as an initial force in advance;

increase or decrease the initial force so that the tactile force sense required to be provided is provided to the user via the fitting member on providing the tactile force sense, when the tactile force sense required to be provided is not able to be produced by a resultant force combining one or more forces in pulling directions, resets direction and magnitude of the tactile force sense required to be provided, the direction and magnitude of the tactile force sense being able to be represented by combination of one or more forces in pulling directions, and increases or decreases the initial force to provide the tactile force sense being reset and, when the user inputs an operation via the operation input unit, output a signal in accordance with the input operation.

2. The tactile force sense providing apparatus according to claim 1, further comprising:

three or more of the conveyance members; and three or more of the drive units each of which corresponds to one of the plurality of the conveyance members, wherein each of the conveyance members is string-like member that extends from different positions of the own apparatus to the fitting member attached on the user, each of the drive units, by winding in the corresponding conveyance member, provides the force in the pulling direction to the corresponding conveyance member, to provide the tactile force sense by a resultant force of one or more forces in the pulling directions that are provided to the conveyance members, and the control unit is further configured, when the tactile force sense required to be provided is not able to be produced by the resultant force combining one or more forces in pulling directions, to select two conveyance members that are able to generate a resultant force of two forces in the pulling directions, direction of the resultant force of the two conveyance members being nearest to direction of a combined force of the initial force and a tactile force representing the tactile force sense required to be provided, to project the combined force onto a plane that is formed by the two conveyance members being selected, and to reset direction and magnitude of the tactile force sense required to be provided to represent the combined force being projected onto the plane.

3. The tactile force sense providing apparatus according to claim 2, wherein at least one of the plurality of the conveyance members functions as wiring connecting the operation input unit to the control unit.

4. The tactile force sense providing apparatus according to claim 1, wherein the operation input unit is any one of a switch, an acceleration sensor, a magnetic sensor, and a pressure sensor.

5. An information terminal that is capable of providing a tactile force sense to a user in accordance with details of a content displayed on a screen, comprising:

a display apparatus that is configured to display the content on the screen;

a position detection unit that is configured to detect a position of a portion of the user that receives the tactile force sense to be provided;

an information processing unit that is configured to change details of the content in accordance with the detected position and, on the basis of the changed details of the content, to calculate a tactile force sense required to be provided; and a tactile force sense providing apparatus, the tactile force sense providing apparatus comprising:
a fitting member that is formed so as to be attached on a portion of the user that receives the tactile force sense to be provided and comprises an operation input unit that is configured to input an operation performed by the user;

a conveyance member that is configured to extend from the information terminal to the fitting member and to convey a force in a pulling direction to the user via the fitting member;

a drive unit that is configured to produce the force in the pulling direction and to provide the produced force to the conveyance member; and a control unit that is configured to:
produce the force in the pulling direction of a preset magnitude as an initial force to the drive unit in advance, increase or decrease the initial force so that the calculated tactile force sense is provided to the user via the fitting member on providing the tactile force sense calculated by the information processing unit, when the tactile force sense required to be provided is not able to be produced by a resultant force combining one or more forces in pulling directions, resets direction and magnitude of the tactile force sense required to be provided, the direction and magnitude of the tactile force sense being able to be represented by combination of one or more forces in pulling directions, and increases or decreases the initial force to provide the tactile force sense being reset, and when the user inputs an operation via the operation input unit, output a signal in accordance with the input operation to the information processing unit, and, the information processing unit changing details of the content in accordance with details of the signal, when the control unit outputs the signal.

6. The information terminal according to claim 5, further comprising:

three or more of the conveyance members; and three or more of the drive units each of which corresponds to one of the plurality of the conveyance members, wherein each of the conveyance members is string-like member that extends from different positions of the information terminal to the fitting member fitted on the user, each of the drive units, by widing in the corresponding conveyance member, provides the force in the pulling direction to the corresponding conveyance member, to provide the tactile force sense by a resultant force of one or more forces in the pulling directions that are provided to the conveyance members, and the control unit is further configured, when the tactile force sense required to be provided is not able to be produced by the resultant force combining one or more forces in pulling directions, to select two conveyance members that are able to generate a resultant force of two forces in the pulling directions, direction of the resultant force of the two conveyance members being nearest to direction of a combined force of the initial force and a tactile force representing the tactile force sense required to be provided, to project the combined force onto a plane that is formed by the two conveyance members being selected, and to reset direction and magnitude of the tactile force sense required to be provided to represent the combined force being projected onto the plane.

7. The information terminal according to claim 6, wherein at least ones of the plurality of the conveyance members functions as wiring connecting the operation input unit to the control unit.

8. The information terminal according to claim 5, wherein the operation input unit is any one of a switch, an acceleration sensor, a magnetic sensor, and a pressure sensor.

9. A tactile force sense providing method to provide a tactile force sense to a user in accordance with details of a content displayed on a screen, the method comprising by using an apparatus comprising a fitting member that is formed so as to be attached on a portion of the user that receives the tactile force sense to be provided and comprises an operation input unit to input an operation performed by the user, a conveyance member that extends to the fitting member and conveys a force in a pulling direction to the user, and a drive unit that produces the force in the pulling direction and provides the produced force to the conveyance member:

producing a force in a pulling direction of a preset magnitude to the drive unit as an initial force in advance;

increasing or decreasing the initial force so that the tactile force sense to be provided is provided to the user via the fitting member on providing the tactile force sense;

when the tactile force sense required to be provided is not able to be produced by a resultant force combining one or more forces in pulling directions, resetting direction and magnitude of the tactile force sense required to be provided, the direction and magnitude of the tactile force sense being able to be represented by combination of one or more forces in pulling directions, and increasing or decreasing the initial force to provide the tactile force sense being reset; and when the user inputs an operation via the operation input unit, outputting a signal in accordance with the input operation.

10. The tactile force sense providing method of claim 9, further comprising:

by using the apparatus further comprising three or more of the conveyance members and three or more of the drive units each of which corresponds to one of the plurality of the conveyance members, wherein each of the conveyance members is string-like member that extends from different positions of the own apparatus to the fitting member attached on the user, each of the drive units, by winding in the corresponding conveyance member, provides the force in the pulling direction to the corresponding conveyance member, to provide the tactile force sense by a resultant force of one or more forces in the pulling directions that are provided to the conveyance members:

when the tactile force sense required to be provided is not able to be produced by the resultant force combining one or more forces in pulling directions, selecting two conveyance members that are able to generate a resultant force of two forces in the pulling directions, direction of the resultant force of the two conveyance members being nearest to direction of a combined force of the initial force and a tactile force representing the tactile force sense required to be provided, projecting the combined force onto a plane that is formed by the two conveyance members being selected, and resetting direction and magnitude of the tactile force sense required to be provided to represent the combined force being projected onto the plane.

11. A computer-readable recording medium storing a program comprising instructions for a computer, the computer being included in an apparatus to provide a tactile force sense to a user in accordance with details of a content displayed on a screen, the apparatus comprising a fitting member that is formed so as to be attached on a portion of the user that receives the tactile force sense to be provided and includes an operation input unit to input an operation performed by the user, a conveyance member that extends to the fitting member and conveys a force in a pulling direction to the user, a drive unit that produces the force in the pulling direction and provides the produced force to the conveyance member, and the computer, the program allowing the computer to execute:

processing of producing a force in a pulling direction of a preset magnitude to the drive unit as an initial force in advance;

processing of increasing or decreasing the initial force so that the tactile force sense to be provided is provided to the user via the fitting member on providing the tactile force sense;

processing of, when the tactile force sense required to be provided is not able to be produced by a resultant force combining one or more forces in pulling directions, resetting direction and magnitude of the tactile force sense required to be provided, the direction and magnitude of the tactile force sense being able to be represented by combination of one or more forces in pulling directions, and increasing or decreasing the initial force to provide the tactile force sense being reset; and processing of, when the user inputs an operation via the operation input unit, outputting a signal in accordance with the input operation.

12. The computer-readable recording medium of claim 11, wherein the apparatus further comprises three or more of the conveyance members and three or more of the drive units each of which corresponds to one of the plurality of the conveyance members, wherein each of the conveyance members is string-like member that extends from different positions of the own apparatus to the fitting member attached on the user, each of the drive units, by winding in the corresponding conveyance member, provides the force in the pulling direction to the corresponding conveyance member, to provide the tactile force sense by a resultant force of one or more forces in the pulling directions that are provided to the conveyance members; and wherein the program allowing the computer to execute:
processing of, when the tactile force sense required to be provided is not able to be produced by the resultant force combining one or more forces in pulling directions, processing of selecting two conveyance members that are able to generate a resultant force of two forces in the pulling directions, direction of the resultant force of the two conveyance members being nearest to direction of a combined force of the initial force and a tactile force representing the tactile force sense required to be provided, processing of projecting the combined force onto a plane that is formed by the two conveyance members being selected, and processing of resetting direction and magnitude of the tactile force sense required to be provided to represent the combined force being projected onto the plane.

* * * * *